(12) United States Patent
Tischendorf et al.

(10) Patent No.: US 9,398,901 B2
(45) Date of Patent: Jul. 26, 2016

(54) MINIMALLY INVASIVE IMPLANTABLE NEUROSTIMULATION SYSTEM

(71) Applicant: Medtronic, Inc., Minneapolis, MN (US)

(72) Inventors: Brad C. Tischendorf, Minneapolis, MN (US); John E. Kast, Hugo, MN (US); Thomas P. Miltich, Otsego, MN (US); Gordon O. Munns, Stacy, MN (US); Randy S. Roles, Elk River, MN (US); Craig L. Schmidt, Eagan, MN (US); Joseph J. Viavattine, Vadnais Heights, MN (US); Christian S. Nielsen, River Falls, WI (US); Prabhakar A. Tamirisa, Brooklyn Park, MN (US); Anthony M. Chasensky, St. Paul, MN (US); Markus W. Reiterer, Plymouth, MN (US); Chris J. Paidosh, Minneapolis, MN (US); Reginald D. Robinson, Plymouth, MN (US); Bernard Q. Li, Plymouth, MN (US); Erik R. Scott, Maple Grove, MN (US); Phillip C. Falkner, Minneapolis, MN (US); Xuan K. Wei, Minnetonka, MN (US); Eric H. Bonde, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/099,462

(22) Filed: Dec. 6, 2013

(65) Prior Publication Data
US 2014/0163646 A1    Jun. 12, 2014

Related U.S. Application Data

(60) Provisional application No. 61/734,436, filed on Dec. 7, 2012, provisional application No. 61/777,787, filed on Mar. 12, 2013, provisional application No. 61/734,425, filed on Dec. 7, 2012, provisional (Continued)

(51) Int. Cl.
*A61N 1/372* (2006.01)
*A61B 17/00* (2006.01)

(Continued)

(52) U.S. Cl.
CPC ............ *A61B 17/00234* (2013.01); *A61N 1/02* (2013.01); *A61N 1/05* (2013.01);
(Continued)

(58) Field of Classification Search
CPC ............... A61B 17/00234; A61N 1/05; A61N 1/36139; A61N 1/37205; A61N 1/37247; A61N 1/37252; A61N 1/36057; A61N 1/3787; A61N 1/3727; A61N 1/375; A61N 1/3754; A61N 1/3756; A61N 1/02; A61N 1/36021; A61N 1/3605; A61N 1/36053; A61N 1/36067; A61N 1/36071; A61N 1/37211; A61N 1/37223; A61N 1/37235
USPC ...................... 607/36, 60, 116–118
See application file for complete search history.

(56) References Cited

U.S. PATENT DOCUMENTS 3,971,388 A * 7/1976 Cowdery ................... 607/36
6,051,017 A * 4/2000 Loeb et al. ................. 607/1

(Continued)

FOREIGN PATENT DOCUMENTS

CN   101522256 A   9/2009
CN   101522260 A   9/2009

(Continued)

OTHER PUBLICATIONS

International Search Report and Written Opinion of Counterpart International Application No. PCT/US2013/073669, dated Apr. 9, 2014, 9 pp.

(Continued)

*Primary Examiner* — Mark W Bockelman
(74) *Attorney, Agent, or Firm* — Shumaker & Sieffert, P.A.

(57) ABSTRACT

An implantable medical device (IMD) has a housing enclosing an electronic circuit. The housing includes a first housing portion, a second housing portion and a joint coupling the first housing portion to the second housing portion. A polymer enclosure member surrounds the joint and circumscribes the housing in various embodiments. Other embodiments of an IMD housing are disclosed.

24 Claims, 21 Drawing Sheets

Related U.S. Application Data application No. 61/777,804, filed on Mar. 12, 2013, provisional application No. 61/734,429, filed on Dec. 7, 2012, provisional application No. 61/777,949, filed on Mar. 12, 2013, provisional application No. 61/734,446, filed on Dec. 7, 2012, provisional application No. 61/777,824, filed on Mar. 12, 2013, provisional application No. 61/777,838, filed on Mar. 12, 2013.

(51) Int. Cl.
| | |
|---|---|
| A61N 1/05 | (2006.01) |
| A61N 1/36 | (2006.01) |
| A61N 1/378 | (2006.01) |
| A61N 1/02 | (2006.01) |
| A61N 1/375 | (2006.01) |

(52) U.S. Cl.
CPC ............... *A61N 1/0551* (2013.01); *A61N 1/36* (2013.01); *A61N 1/3605* (2013.01); *A61N 1/36057* (2013.01); *A61N 1/36139* (2013.01); *A61N 1/3727* (2013.01); *A61N 1/3754* (2013.01); *A61N 1/3787* (2013.01); *A61N 1/37205* (2013.01); *A61N 1/37235* (2013.01); *A61N 1/37247* (2013.01); *A61N 1/37252* (2013.01); *A61N 1/36007* (2013.01); *A61N 1/36021* (2013.01); *A61N 1/36053* (2013.01); *A61N 1/36067* (2013.01); *A61N 1/36071* (2013.01); *A61N 1/375* (2013.01); *A61N 1/3756* (2013.01); *A61N 1/37211* (2013.01); *A61N 1/37223* (2013.01)

(56) References Cited

U.S. PATENT DOCUMENTS

| | | | | |
|---|---|---|---|---|
| 6,975,906 | B2 * | 12/2005 | Rusin et al. | 607/36 |
| 7,103,415 | B2 * | 9/2006 | Probst et al. | 607/36 |
| 7,467,014 | B2 * | 12/2008 | Fuller et al. | 607/60 |
| 8,989,861 | B2 | 3/2015 | Su et al. | |
| 2003/0114905 | A1 | 6/2003 | Kuzma | |
| 2005/0021119 | A1 | 1/2005 | Sage et al. | |
| 2005/0092507 | A1 | 5/2005 | Marshall et al. | |
| 2006/0085041 | A1 | 4/2006 | Hastings et al. | |
| 2007/0123923 | A1 | 5/2007 | Lindstrom et al. | |
| 2007/0156204 | A1 | 7/2007 | Denker et al. | |
| 2008/0058871 | A1 | 3/2008 | Libbus et al. | |
| 2008/0086181 | A1 | 4/2008 | Amurthur et al. | |
| 2009/0118778 | A1 | 5/2009 | Biggs, Jr. et al. | |
| 2009/0149900 | A1 | 6/2009 | Moffitt et al. | |
| 2009/0157147 | A1 | 6/2009 | Cauller et al. | |
| 2010/0023102 | A1 | 1/2010 | Spruit | |
| 2010/0106223 | A1 | 4/2010 | Grevious et al. | |
| 2010/0152808 | A1 | 6/2010 | Boggs, II | |
| 2011/0301670 | A1 | 12/2011 | Gross et al. | |
| 2012/0130398 | A1 | 5/2012 | Ackermann et al. | |
| 2012/0303105 | A1 | 11/2012 | Askarinya et al. | |

FOREIGN PATENT DOCUMENTS

| | | |
|---|---|---|
| CN | 101528303 A | 9/2009 |
| WO | 2004002572 A1 | 1/2004 |
| WO | 2009134466 A1 | 11/2009 |
| WO | 2010059096 A1 | 5/2010 |

OTHER PUBLICATIONS

U.S. Appl. No. 14/098,608, filed Dec. 6, 2013, by Tischendorf et al.
U.S. Appl. No. 14/098,621, filed Dec. 6, 2013, by Tischendorf et al.
U.S. Appl. No. 14/098,672, filed Dec. 6, 2013, by Scott et al.
U.S. Appl. No. 14/098,728, filed Dec. 6, 2013, by Dinsmoor et al.
International Preliminary Report on Patentability from counterpart International Application No. PCT/US2013/073669, dated Jun. 18, 2015, 7 pp.
First Office Action, and translation thereof, from counterpart Chinese Patent Application No. 201380060948.X, dated Dec. 22, 2015, 12 pp.

* cited by examiner

MINIMALLY INVASIVE IMPLANTABLE NEUROSTIMULATION SYSTEM

CROSS-REFERENCE TO RELATED APPLICATIONS

The present application claims priority to U.S. Provisional Patent Application No. 61/734,425, filed Dec. 7, 2012, which application is incorporated herein by reference as if re-written in its entirety.

The present application claims priority to U.S. Provisional Patent Application No. 61/777,804, filed Mar. 12, 2013, which application is incorporated herein by reference as if re-written in its entirety.

The present application claims priority to U.S. Provisional Patent Application No. 61/734,429, filed Dec. 7, 2012, which application is incorporated herein by reference as if re-written in its entirety.

The present application claims priority to U.S. Provisional Patent Application No. 61/777,949, filed Mar. 12, 2013, which application is incorporated herein by reference as if re-written in its entirety.

The present application claims priority to U.S. Provisional Patent Application No. 61/734,446, filed Dec. 7, 2012, which application is incorporated herein by reference as if re-written in its entirety.

The present application claims priority to U.S. Provisional Patent Application No. 61/777,824, filed Mar. 12, 2013, which application is incorporated herein by reference as if re-written in its entirety.

The present application claims priority to U.S. Provisional Patent Application No. 61/777,838, filed Mar. 12, 2013, which application is incorporated herein by reference as if re-written in its entirety.

The present application claims priority to U.S. Provisional Patent Application No. 61/734,436, filed Dec. 7, 2012, which application is incorporated herein by reference as if re-written in its entirety.

The present application claims priority to U.S. Provisional Patent Application No. 61/777,787, filed Mar. 12, 2013, which application is incorporated herein by reference as if re-written in its entirety.

FIELD OF THE DISCLOSURE

The disclosure relates generally to implantable neurostimulation systems and in particular to minimally invasive neurostimulation systems.

SUMMARY

An implantable medical device (IMD) of a neurostimulation system includes an electronic circuit, a housing enclosing the electronic circuit and including a first housing portion, a second housing portion and a joint coupling the first housing portion to the second housing portion, and a polymer enclosure member surrounding the joint. The polymer enclosure member may include a protruding structure to facilitate fixation of the medical device in various embodiments. An electrode may be provided along an outer surface of the housing.

The IMD includes a conductive coil for receiving inductively coupled energy in some embodiments. The coil may be positioned around an exterior surface of the first housing portion and electrically coupled to the electronic circuit with the polymer enclosure member surrounding the coil. A mandrel may be positioned around the first housing portion exterior surface, and the coil positioned around the mandrel. In other embodiments, the polymer enclosure may include a first polymer enclosure member surrounding the joint and a second polymer enclosure member surrounding the first polymer enclosure and the coil. The coil may be positioned around an exterior surface of the first polymer enclosure. An electrode coupled to the housing may be exposed through the second enclosure member.

The IMD housing may include an end cap assembly coupled to an end of the first housing portion and the second housing portion mated along the joint to define an interior cavity to enclose the electronic circuit. In one example, the first housing portion and the second housing portion each include a pair of opposing minor sidewalls separated by a major sidewall. The pairs of opposing minor sidewalls of each of the first housing portion and the second housing portion are configured to mate along the joint. The end cap assembly is coupled to the mated housing portions. A conductive coil for receiving inductively coupled energy may extend around an exterior surface of the first housing portion, and the end cap assembly may include an electrical feedthrough coupled to the electronic circuit and to the conductive coil. The polymer enclosure may surround the conductive coil and the joint. The polymer enclosure may be provided with an aperture for exposing a connection between the conductive coil and the electrical feedthrough to enable welding of the connection.

In another embodiment, an implantable medical device includes an electronic circuit and a housing enclosing the electronic circuit. The housing includes a joint and a polymer enclosure member circumscribing the housing, surrounding the joint.

In yet another embodiment, a method for assembling an implantable medical device includes enclosing an electronic circuit within a housing having a first housing portion, a second housing portion and a joint coupling the first housing portion to the second housing portion, and surrounding the joint with a polymer enclosure member such that the polymer enclosure circumscribes the housing. These and other embodiments are described herein.

DETAILED DESCRIPTION

Applicants have an appreciation that implantable medical device (IMD) technology is continually advancing as new applications are developed for automated therapy delivery in patients. Such advances may be further enhanced by using devices of reduced size and weight, which makes implantation of such devices less invasive and chronic use more comfortable for the patient. Additionally, applicants recognize that such enhancements such as improved power supply systems, wireless telemetry systems for communication with the implanted device, tools for performing implantation procedures, apparatus and methods for targeting a delivered therapy at desired location, and other system improvements can also enhance therapies in a manner that saves cost, conserves energy and minimizes any burden placed on the patient or clinician. Accordingly, Applicants recognize a need for improved, minimally-invasive implantable medical device systems and associated methods of use for providing patient monitoring and/or therapy delivery. Certain exemplary embodiments disclosed herein may obtain some or all of the aforementioned advantages and enhancements.

In the following description, references are made to illustrative embodiments. Various embodiments of a housing for an IMD included in an implantable neurostimulation (INS) system for delivering an electrical stimulation therapy to a targeted neural site are described. However, it is recognized that the various embodiments of the housings described herein may be implemented in numerous types of IMDs, including, for example, implantable sensors, implantable communication devices, and other types of implantable therapy delivery systems. The various embodiments of IMD housings described herein and associated methods of manufacture will reduce size and/or cost of the device and promote and facilitate minimally invasive implantation procedures in which the incision size and time required to implant and anchor the device can be minimized.

Figure 1:
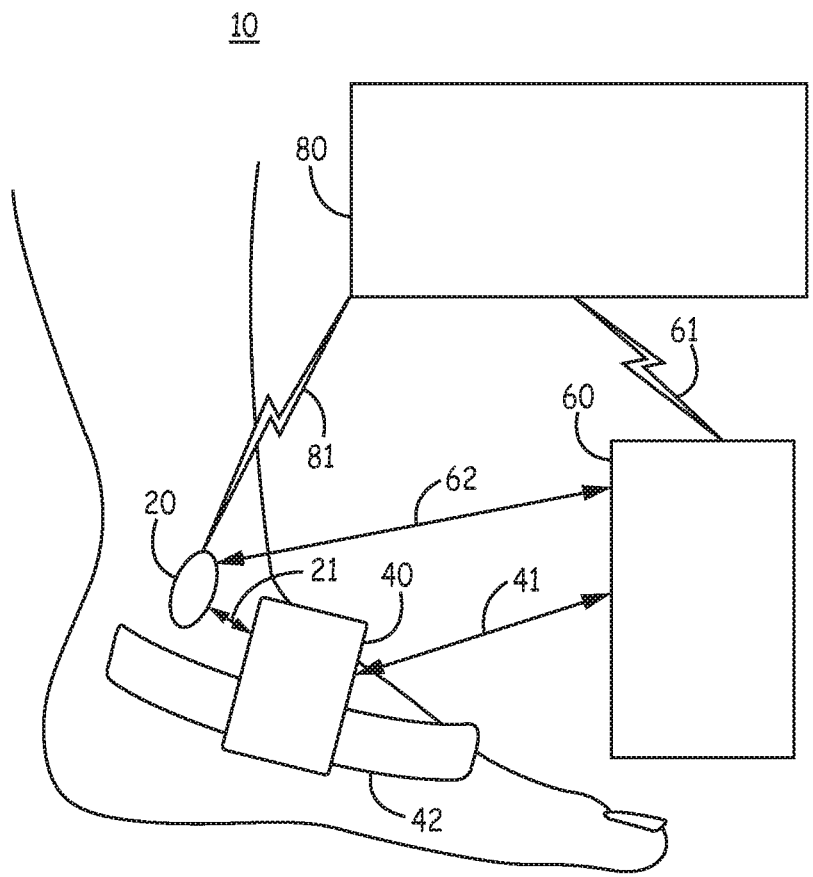
FIG. 1 is a schematic diagram of an exemplary minimally invasive IMD system capable of delivering a neurostimulation therapy.
Figure 1:
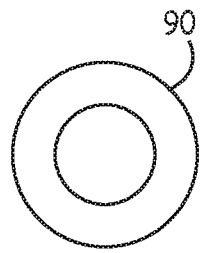

FIG. 1 is a schematic diagram of a minimally invasive INS system 10 capable of delivering a neurostimulation therapy. System 10 includes an IMD 20, an external device 40 enabled for transmitting signals to IMD 20, a patient programming device 60 enabled for bidirectional communication with IMD 20 and/or external device 40, and a physician programming device 80 according to an illustrative embodiment. In the illustrative embodiments described herein, communication between components included in the INS system 10 is configured to be bidirectional communication, however it is recognized that in some embodiments communication between two or more system components may be unidirectional.

IMD 20 includes circuitry for delivering neurostimulation pulses enclosed in a sealed housing and coupled to therapy delivery electrodes. In various embodiments, IMD 20 may include one or more of a primary battery cell, a rechargeable battery cell, and an inductively coupled power source for providing power for generating and delivering stimulation pulses and powering other device functions such as communication functions.

In some embodiments, IMD 20 is less than approximately 30 mm in length, or less than approximately 15 mm in length, and less than approximately 1 cc in volume. In illustrative embodiments, the term "approximately" as used herein may indicate a value of ±10% of a stated value and may correspond to a range of manufacturing specification tolerances. In other examples, IMD 20 may be less than approximately 10 mm in length and may be less than approximately 0.6 cc in volume. IMD 20 may be approximately 0.1 cc in volume in some embodiments. The embodiments described herein are not limited to a particular size and volume of IMD 20, but are generally implemented to enable the use of a reduced size device for minimally invasive implantation procedures and minimized discomfort to a patient. It is recognized, however, that the various IMD systems described herein may be implemented in conjunction with a wide variety of IMD sizes and volumes adapted for a particular therapy or monitoring application.

External device 40 may be a wearable device including a strap 42 or other attachment member(s) for securing external device 40 to the patient in operable proximity to IMD 20. When IMD 20 is provided with rechargeable battery cell(s), external device 40 may be embodied as recharging unit for transmitting power, for example inductive power transmission from external device 40 to IMD 20. In this embodiment, programming device 60 may be a patient handheld device that is used to initiate and terminate therapy delivered by IMD 20 via a bidirectional wireless telemetry link 62. Alternatively, programming device 60 could be operated by a patient for communicating with wearable external device 40 via wireless link 41 to control therapy on and off times and other therapy control parameters, which are transmitted to IMD 20 via communication link 21. Programming device 60 may communicate with wearable external device 40 via a bidirectional wireless telemetry link 41 that may establish communication over a distance of up to a few feet or more, enabling distance telemetry such that the patient need not position programming device 60 directly over IMD 20 to control therapy on and off times or perform other interrogation or programming operations (e.g., programming of other therapy control parameters).

When IMD 20 includes primary cell(s) a wearable external device 40 may be optional. Programming of IMD 20 may be performed by the programming device 60, using near- or distance-telemetry technology for establishing bidirectional communication link 62 for transmitting data between programmer 60 and IMD 20. Programming device 60 may be used by a patient or clinician to set a therapy protocol that is performed automatically by IMD 20. Programming device 60 may be used to manually start and stop therapy, adjust therapy delivery parameters, and collect data from IMD 20, e.g. data relating to total accumulated therapy delivery time or other data relating to device operation or measurements taken by IMD 20.

When IMD 20 is configured as an externally powered device, external device 40 may be a power transmission device that is worn by the patient during a therapy session to provide power needed to generate stimulation pulses. For example, external device 40 may be a battery powered device including a primary coil used to inductively transmit power to a secondary coil included in IMD 20. External device 40 may include one or more primary and/or rechargeable cells and therefore may include a power adaptor and plug for re-charging in a standard 110V or 220V wall outlet, for example.

It is contemplated that in some embodiments the functionality required for transmitting power to IMD 20 when IMD 20 is embodied as a rechargeable or externally powered device and for programming the IMD 20 for controlling therapy delivery may be implemented in a single external device. For example, power transmission capability of external device 40 and programming capabilities of patient programmer 60 may be combined in a single external device, which may be a wearable or handheld device.

Physician programming device 80 may include increased programming and diagnostic functionality compared to patient programming device 60. For example, physician programming device 80 may be configured for programming all neurostimulation therapy control parameters, such as but not limited to pulse amplitude, pulse width, pulse shape, pulse frequency, duty cycle, and therapy on and off times. Patient programming device 60 may be limited to turning therapy on and/or off, adjusting a start time of therapy, and/or adjusting a pulse amplitude without giving access to the patient to full programming functions such that some programming functions and programmable therapy control parameters cannot be accessed or altered by a patient.

Physician programming device 80 may be configured to communicate directly with IMD 20 via wireless, bidirectional telemetry link 81, for example during an office visit. Additionally or alternatively, physician programming device 80 may be operable as remote programming instrument used to transmit programming commands to patient programming device 60 via a wired or wireless communication network link 61, after which patient programming device 60 automatically transmits programming data to IMD 20 via bidirectional telemetry link 62 (or via wearable external device 40 and link 21).

In some embodiments, the patient may be provided with a magnet 90 for adjusting operation of IMD 20. For example, application of magnet 90 may turn therapy on or off or cause other binary or stepwise adjustments to IMD 20 operations.

While IMD 20 is shown implanted along a portion of the lower leg of a patient, IMD 20 could be implanted at numerous sites according to patient need and the particular medical application. In the illustrative embodiment, IMD 20 is provided for stimulating the tibial nerve of the patient to treat overactive bladder syndrome and is merely one example of the type of medical application for which INS system 10 may be used. In another example, IMD 20 may be implanted to deliver a stimulation therapy to muscles of the pelvic floor, such as periurethral muscles or the external uretheral sphincter for treating symptoms of urinary incontinence or overactive bladder syndrome. In other examples, IMD 20 may be deployed for delivering neurostimulation therapy to an acupuncture point for treatment of a symptom associated with the acupuncture point. IMD 20 may be implemented in an INS system for providing numerous types of neurostimulation therapies, such as for pain control, autonomic nervous system modulation, tremor, functional electrical stimulation, and more.

Figure 2:
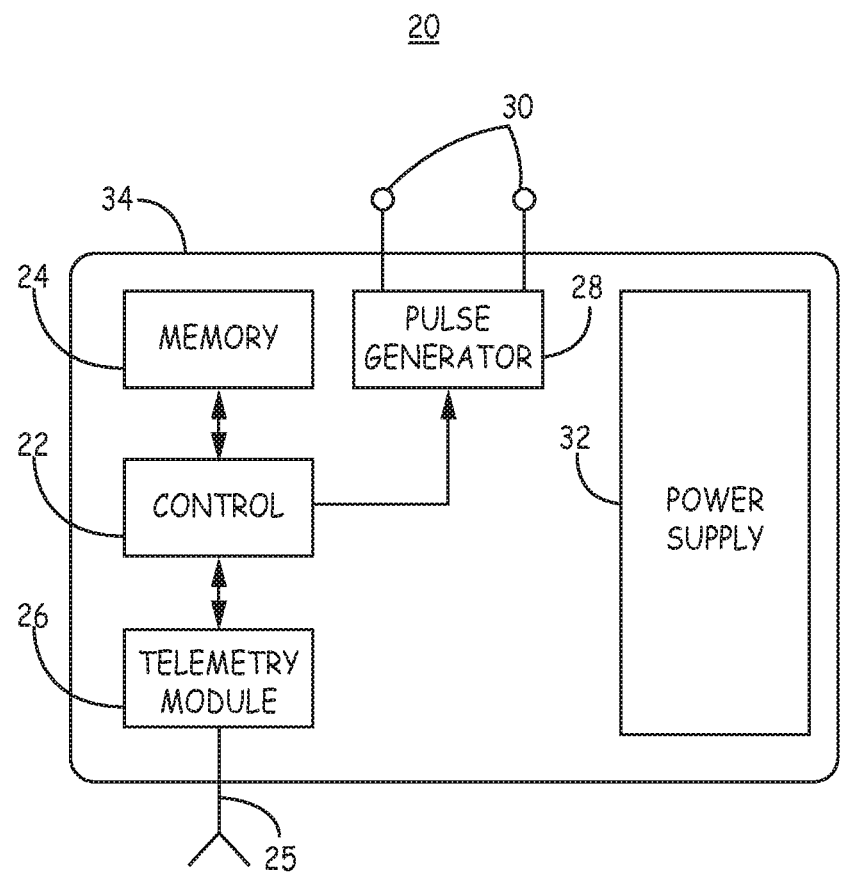
FIG. 2 is a functional block diagram of the IMD shown in FIG. 1 according to one embodiment.

FIG. 2 is a functional block diagram of IMD 20 according to one embodiment. IMD 20 includes a housing 34 enclosing a control unit 22 and associated memory 24, a telemetry module 26, and a pulse generator 28 coupled to electrodes 30. IMD 20 includes a power supply 32, which as described above may include any of a primary battery cell, a rechargeable battery cell, and/or a secondary coil of an externally powered system.

Control unit 22 may include any one or more of a microprocessor, a controller, a digital signal processor (DSP), an application specific integrated circuit (ASIC), a field-programmable gate array (FPGA), or equivalent discrete or integrated logic circuitry. In some examples, control unit 22 may include multiple components, such as any combination of one or more microprocessors, one or more controllers, one or more DSPs, one or more ASICs, or one or more FPGAs, as well as other discrete or integrated logic circuitry. The functions attributed to control unit 22 herein may be embodied as software, firmware, hardware or any combination thereof. In one example, a neurostimulation therapy protocol may be stored or encoded as instructions in memory 24 that are executed by control unit 22 to cause pulse generator 28 to deliver the therapy via electrode 30 according to the programmed protocol.

Memory 24 may include computer-readable instructions that, when executed by control unit 22, cause IMD 20 to perform various functions attributed throughout this disclosure to IMD 20. The computer-readable instructions may be encoded within memory 24. Memory 24 may comprise non-transitory computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media with the sole exception being a transitory propagating signal.

Telemetry module 26 and associated antenna 25 are provided for establishing bidirectional communication with wearable external device 40, patient programmer 60 and/or physician programmer 80. Examples of communication techniques used by IMD 20 and external device 40, patient programmer 60 and/or physician programmer 80 include low frequency or radiofrequency (RF) telemetry, which may be an RF link established via Bluetooth, WiFi, or MICS, for example. Antenna 25 may be located within, along or extend externally from housing 34.

Electrodes 30 may be located along an exterior surface of housing 34 and are coupled to pulse generator 28 via insulated feedthroughs or other connections as will be further described below. In other embodiments, electrodes 30 may be carried by a lead or insulated tether electrically coupled to pulse generator 28 via appropriate insulated feedthroughs or other electrical connections crossing sealed housing 34. In still other embodiments, electrodes 30 may be incorporated in housing 34 with externally exposed surfaces adapted to be operably positioned in proximity to a targeted nerve and electrically coupled to pulse generator 28.

Figure 3:
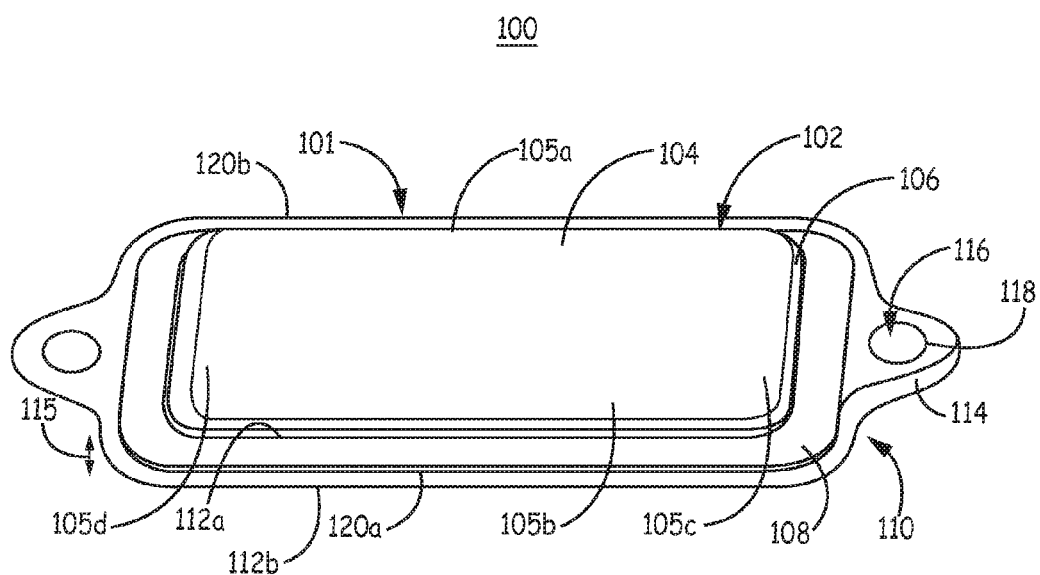
FIG. 3 is a perspective view of one exemplary embodiment of an IMD that may be implemented in an implantable neurostimulation (INS) system.

FIG. 3 is a perspective view of one embodiment of an IMD 100 that may be implemented in an INS system. IMD 100 includes a first housing portion 102 sealed to a second housing portion not seen in the perspective view of FIG. 3. The first housing portion 102 includes a top face 104, extending between lateral edges 105a and 105b and end edges 105c and 105d, and a continuous side wall 106 extending at an angle less than 180 degrees from top face 104 along each of sides 105a through 105d. Top face 104 and side wall 106 define an internal cavity for housing IMD electronics. In one example, top face 104 and side wall 106 extend substantially perpendicular to each other but may form a larger or smaller angle with respect to each other. Furthermore, it is contemplated that edges 105a-105d and side wall 106 may be rounded or chamfered to provide a smooth continuous surface without sharp corners or edges that would potentially cause patient discomfort.

Housing portion 102 further includes flange 108 extending from side wall 106 along at least a portion of side wall 106. In the embodiment shown, flange 108 is a continuous flange circumscribing side wall 106 and extending laterally outward from the internal cavity formed by top face 104 and side wall 106. Flange 108 may extend substantially parallel to top face 104 and provides a flat surface that becomes sealed to the second housing portion to define a sealed cavity within the housing for containing IMD electronics. Housing portion 102 may be formed of a biocompatible metal such as titanium (e.g., grade 1, 5, 9 or 23), stainless steel (e.g., type 304 or type 316), MP35N, niobium, tantalum, platinum, iridium, or any combination or alloys thereof.

Housing 101 includes a polymer enclosure 110 that surrounds at least the exterior of flange 108 of housing portion 102. Polymer enclosure 110 may be a preformed or over-molded component formed from a biocompatible thermoset or thermoplastic material, such as but not limited to silicone rubber, epoxy, polysulfone, polyurethane, Liquid Crystal Polymer (LCP) or polyether ether ketone (PEEK). Polymer enclosure 110 provides a smooth edge around flange 108 for reducing patient discomfort that may otherwise be caused by flange 108 and for protecting the seal between flange 108 and the second housing portion.

Polymer enclosure 110 may include features for facilitating implantation and/or fixation of IMD 10. In one example, polymer enclosure 110 includes a protruding suture tab 114, which may include a preformed suture hole 116 defined by an inner surface 118 of tab 114. In other embodiments, tab 114 may be a solid portion of enclosure 110 which a suture may be advanced through or wrapped around to facilitate anchoring of IMD 100. In various embodiments, enclosure 110 may include a tab, protrusion, ring, groove, channel or other feature that facilitates securing of a suture or other fixation device to IMD 100 for anchoring IMD 100 at a desired implant site.

Enclosure 110 includes lateral exterior flanges 120a and 120b having top and bottom surfaces 112a and 112b separated by a thickness 115. Flanges 120a and 120b of enclosure 110 function as rails or guides for an implantation tool used to inject IMD 100 at a target implant site. Enclosure flanges 120a and 120b may include one or more ridges, bumps or grooves for aligning and guiding positioning of IMD 100 within an implantation tool upon insertion of IMD 100 into the tool and during ejection of IMD 100 from the tool. For example a syringe body may be configured for receiving IMD 100 with interfacing grooves for receiving flanges 120a and 120b, along which IMD 100 advances when being advanced out of the syringe body using a plunger.

Figure 4:
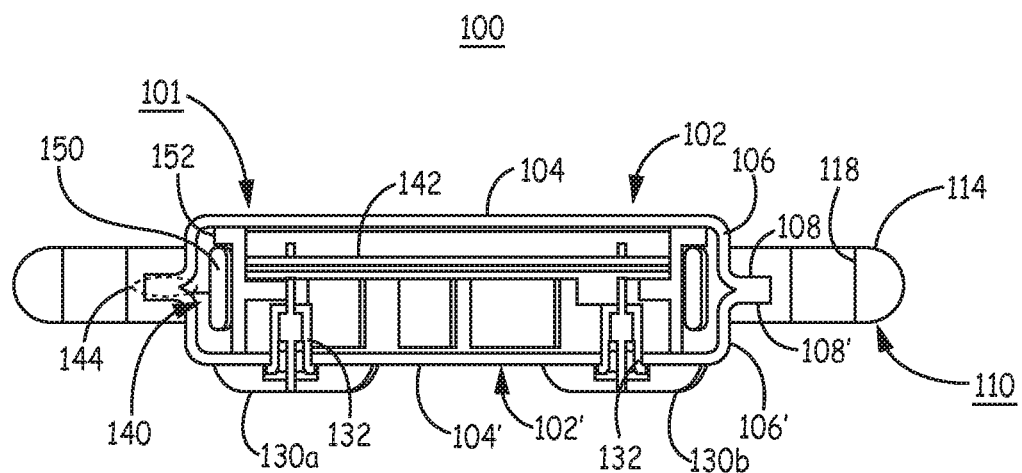
FIG. 4 is a side sectional view of the IMD shown in the perspective view of FIG. 3.

FIG. 4 is a side sectional view of IMD 100 shown in the perspective view of FIG. 3. Housing 101 includes a first housing portion 102 and a second housing portion 102' each having a top face 104 and 104' circumscribed by a side wall 106 and 106' from which respective flanges 108 and 108' extend outwardly from housing portions 102 and 102'. When first and second housing portions 102 and 102' are assembled together, a seal indicated at dashed oval 144 between flanges 108 and 108' is formed by welding or other joining or bonding techniques to seal housing portions 102 and 102' together and thereby enclose a cavity 140 in which IMD electronics 142 are housed. The flanges 108 and 108' meet at a generally flat interface facilitating cost-saving sealing techniques, e.g. roller seam welding, as opposed to laser welding. The flanges 108 and 108' are surrounded by the polymer enclosure 110, having protruding tabs 114. An inner surface 118 of tab 114 defines a suture guide as described previously. Accordingly, in one embodiment, housing portions 102 and 102' are sealed by a roller seam weld or laser welded at seal location 144 between flanges 108 and 108' and the seal is further protected by enclosure 110 to provide a sealed, fluid resistant housing 101 for enclosing circuitry 142.

In the embodiment shown, an inductive coil 150 wound around a supporting bobbin 152 is enclosed in internal cavity 140 defined by housing 101. Electrodes 130a and 130b are shown positioned along the outer top surface 104' of second housing portion 102' and electrically coupled to electronic circuitry 142 via insulated feedthroughs 132. The positioning and connection of electrodes 130a and 130b and coil 150 are illustrative. It is recognized that other electrode configurations and other coil configurations, when coil 150 is present for inductively coupled power transfer, may be used in conjunction with an IMD 100 having a sealed, flanged housing 101 including a polymer enclosure 110.

The cross-sectional shape of IMD 100 is shown to be generally rectangular in FIG. 4 with housing portions 102 and 102' being substantially symmetrical. In alternative embodiments, the housing portions 102 and 102' may be symmetrical and semi-circular such that housing 101 has a substantially circular cross-section or semi-elliptical such that housing 101 has a substantially elliptical cross-section. In still other embodiments, the housing portions 102 and 102' may be asymmetrical. For example, one portion may have a substantially flattened profile or rectangular profile as shown in FIG. 4 and the other portion may have a semi-circular or semi-elliptical cross section resulting in an overall cross-section of housing 101 that is substantially semi-circular or semi-elliptical. The housing 101 and other housings described herein may be adapted to having a variety of polygonal or rounded cross-sectional shapes and profiles to best suit a particular implant site, implantation delivery tool, implantation procedure or other application-specific requirements. For example, an IMD having a semi-circular or semi-elliptical shape or other convex profile may be particularly well-suited for implantation superior to the flexor retinaculum in the posterior region of the medial malleolus for delivering a neurostimulation therapy to the tibial nerve. The anatomical contour of this region includes a concave portion along which a convex portion of the IMD housing may be positioned to naturally conform to the patient's anatomy in a stable, comfortable and unobtrusive manner.

Figure 5:
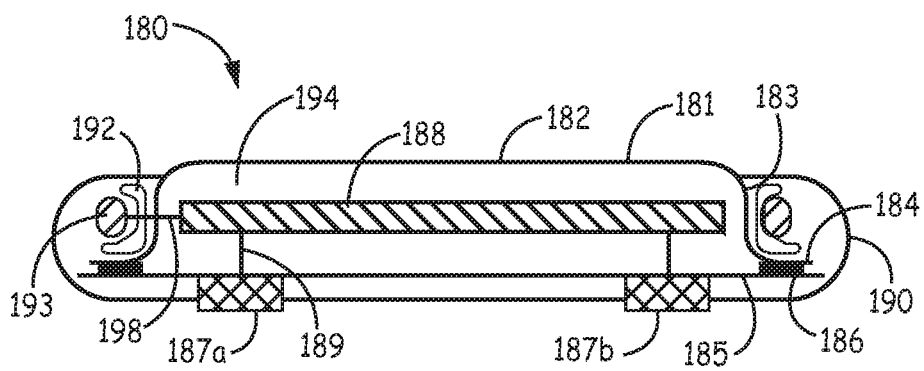
FIG. 5 is a sectional view of a sealed, flanged housing for an IMD according to an alternative exemplary embodiment.

FIG. 5 is a sectional view of a sealed, flanged housing 180 for an IMD according to an alternative embodiment. Housing 180 includes a first portion 181 having a top face 182 circumscribed by a side wall 183 from which flange 184 extends outwardly as described above. Second housing portion 185 is formed as a substantially flat "lid" having an outer dimension such that portion 185 extends at least partially over flange 184. A seam 186 (shown exaggerated in FIG. 5) is formed between flange 184 and the overlapping portion of second housing portion 185, e.g. by roller welding. Accordingly, a sealed, flanged housing is not limited to having two symmetrical housing portions; at least one housing portion has an outwardly extending flange over which a second housing portion extends to at least partially overlap the flange to form a generally flat, laterally-extending interface to facilitate sealing of the two housing portions together, e.g. using roller welding.

In this embodiment, a polymer enclosure 190 surrounds flange 184 and second housing portion 185, extending partially along sidewall 183 of first housing portion but leaving at least a portion of top face 182 exposed. Electrodes 187a and 187b are positioned along the exterior surface of second housing portion 185 and include outer surfaces that are exposed through polymer enclosure 190. Electrodes 187a and 187b are electrically coupled to electronics 188 enclosed within cavity 194 defined by housing 180 via insulated feedthroughs 189.

An inductive coil 193 is embedded in polymer enclosure 190, exterior to housing portion 181. Coil 193 may be wound around a bobbin or mandrel 192 that enables an interconnect of the coil 193 to feedthroughs 198 for electrically coupling coil 193 to electronic circuitry 188 enclosed in housing 180. Mandrel 192 is positioned around housing portion side wall 183 and remains in place when polymer enclosure 190 is overmolded to surround and embed coil 193, the interconnect to feedthrough 198, flange 184 and second housing portion 185. In other embodiments, coil 193 may be positioned around side wall 183 without mandrel 192 being present. Coil 193 may be pre-wound and dropped in around side wall 183 then coil ends welded or otherwise electrically coupled to feedthroughs 198.

Figure 6:
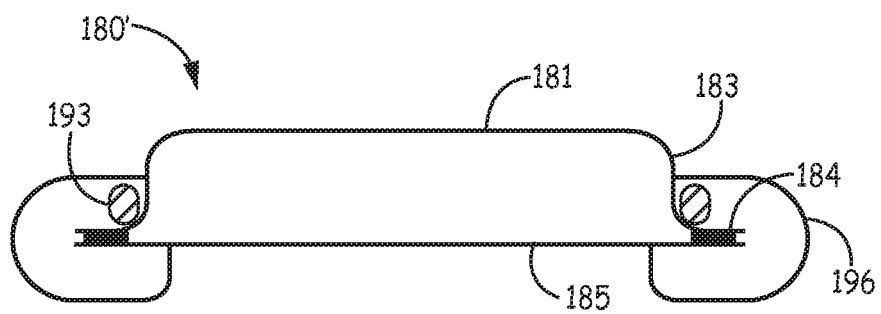
FIG. 6 is a side sectional view of an alternative exemplary embodiment of a sealed, flanged housing.

FIG. 6 is a side sectional view of an alternative embodiment of a sealed, flanged housing 180'. Housing 180' includes a first housing portion 181 having a flange 184 extending outwardly from side wall 183 as described above. Flange 184 is sealed to an overlapping portion of a generally flat second housing portion 185 as described in conjunction with FIG. 5. In this embodiment, a polymer enclosure 196 surrounds flange 184, a portion of sidewall 183 and a portion of second housing portion 185 but does not entirely cover second housing portion 185 as shown and described in conjunction with FIG. 5. A coil 193 may be positioned around side wall 183 and embedded in polymer enclosure 196, with or without a supporting bobbin or mandrel present.

Figure 7:
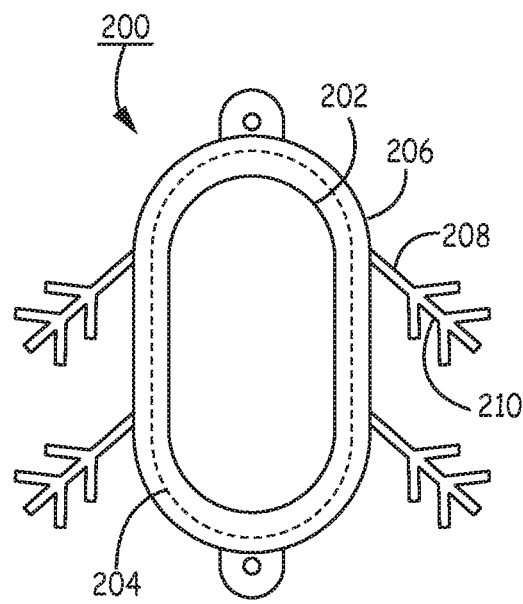
FIG. 7 is a top plan view of an exemplary IMD housing including passive fixation members.

FIG. 7 is a top plan view of an IMD housing 200 including passive fixation members. Housing 200 includes a flanged housing portion 202 sealed to a second housing portion along flange 204 as described above in conjunction with FIGS. 4, 5 and 6. Flange 204 is embedded and surrounded by a polymeric enclosure 206. Enclosure 206 may be pre-molded and stretched to position enclosure 206 around flange 204. When pre-molded, an adhesive coating may be applied between enclosure 206 and flanged housing portion 202. Enclosure 206 may alternatively be an overmolded component, i.e. molded over housing 200.

Enclosure 206 includes passive fixation members 208, shown as one or more tines, each of which may include one or more barbs 210. Enclosure 206 may be molded with fixation members 208 as a single component. Passive fixation members 208 aid in anchoring the IMD at a targeted implant site, reducing the likelihood of shifting or migration of the IMD. Fixation members 208 are not necessarily drawn to scale relative to housing 200 and may have a length that is any relative dimension to the overall dimensions of housing 200. Fixation members 208 may extend from enclosure 206 in any direction relative to housing 200 and may include any arrangement of tines, barbs, hooks, serrations or other protruding structures for engaging surrounding tissue to effectively anchor housing 200 in place.

Figure 8:
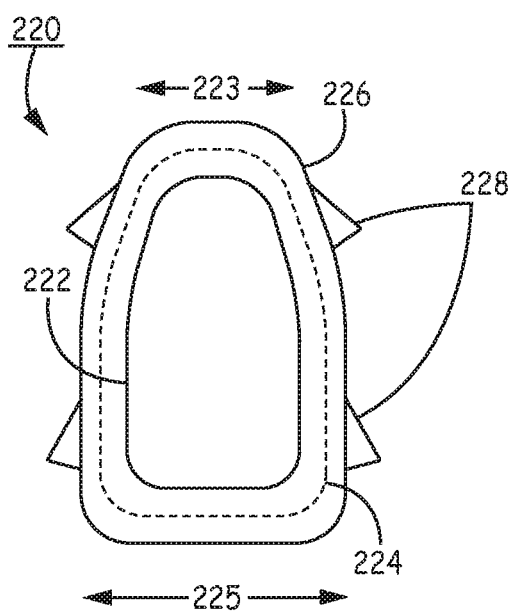
FIG. 8 is a top plan view of an exemplary IMD housing including passive fixation members according to an alternative embodiment.

FIG. 8 is a top plan view of an IMD housing 220 including passive fixation members according to an alternative embodiment. Housing 220 includes a first housing portion 222 having a flange 224 sealed to a second housing portion. Flange 224 is embedded or enclosed in polymer enclosure 226. Enclosure 226 includes barbs 228 extending outward from enclosure 226. Barbs 228 may extend laterally outward, upward, downward or in any desired direction from polymer enclosure 226.

In alternative embodiments, a polymer enclosure enclosing a sealed flange of the IMD housing may include one or more barbs, hooks, tines, tabs, ridges, bumps or other protruding members, or any combination thereof, that encourage or facilitate fixation of the housing at a target location. Protruding members may extend at any angle in any desired direction from any side, i.e. a top, bottom or lateral circumferential surface of the polymer enclosure.

Additionally or alternatively, the polymer enclosure surrounding a sealed flange of the housing may include one or more suture holes, grooves, channels, indentations, perforations, or any other receding or inner surfaces that define guides or openings for placement of sutures, staples, clips, screws, or other active fixation members or enabling tissue ingrowth for stably anchoring the IMD at a targeted implant site. While polymer enclosures incorporating fixation members have been described as extending over a sealed flange of a housing portion it is contemplated that a polymer enclosure may extend over any housing portion, which may or may not include extending over a housing seal, to provide and/or facilitate fixation of the IMD.

Housing 200 of FIG. 7 is shown having a generally rounded rectangular shape. In other embodiments, as shown in FIG. 8, the IMD housing may have a triangular or wedge-type shape that has a narrower width 223 near a first end and a wider width 225 near a second opposing end. In this way, the narrower end of the IMD housing can be readily inserted into a tissue pocket at an implant site as compared to a relatively wider end, and the wider end reduces the likelihood of device migration by fitting more tightly in the device pocket. A barb 228 or other fixation member such as a tine or hook may protrude from enclosure 226 at or near the narrower end and/or at or near the wider end. In other embodiments, the triangular or wedge-type shape housing is used without additional protruding fixation members and the exterior shape is used to passively promote fixation of the IMD.

Figure 9:
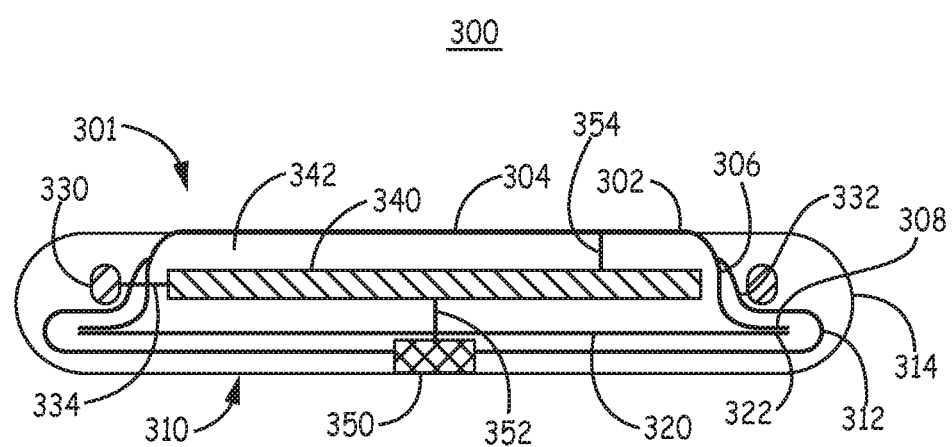
FIG. 9 is a side sectional view of an exemplary IMD including a two-shot molded enclosure according to an alternative embodiment.

FIG. 9 is a side sectional view of an IMD 300 including a two-shot enclosure according to an alternative embodiment. Housing 301 includes a first housing portion 302 having a top face 304 intersecting with a side wall 306. A flange 308 extends laterally outward from side wall 306, substantially parallel to top face 304. Housing 301 includes a second housing portion 320, which is a substantially flat lid that is sealed to flange 308 along an overlapping seal area 322. The sealed first portion and second portion define a cavity 342 enclosing electronic circuitry 340.

A polymer enclosure 310 includes a first shot 312 molded to enclose and embed seal area 322 of flange 308 and second housing portion 320. The first shot 312 may additionally surround and embed a coil 330, which may be wound around a mandrel (not shown in FIG. 9) positioned circumferentially around the exterior surface of housing portion side wall 306. Alternatively, as shown in FIG. 9, the coil 330 is wound around an outer surface 332 of the first shot 312.

An electrical connection between coil 330 and insulated feedthroughs 334 provides electrical coupling of coil 330 to electronic circuitry 340. The first shot 312 at least encompasses and surrounds a seal area 322 and, as shown in FIG. 9, may surround and embed the second housing portion 320 entirely and a portion of side wall 306. The first shot 312 also serves as a coil bobbin or mandrel for supporting coil 330 outside of housing portions 302 and 320. Housing portions 302 and 320, when formed of a conductive metal may reduce inductive coupling between coil 330 and an external primary coil used to transmit power to IMD 300, leading to power losses. By positioning the coil 330 outside housing portions 302 and 320, power losses are mitigated.

Polymer enclosure 310 includes a second shot 314 that encompasses and surrounds at least a portion of the first shot and coil 330. The second shot 314 is shown to surround the first shot entirely and may leave at least a portion of top face 304 exposed. In one embodiment, at least a portion of top face 304 is electrically coupled by conductor 354 to electronics 340 and functions as a stimulation electrode. A second stimulation electrode 350 may extend along the second housing portion 320 and is surrounded by the polymer enclosure 310 leaving an externally exposed surface electrode 350. Second electrode 350 is electrically coupled to internal electronic circuitry 340 by a feedthrough conductor 352. One or more electrodes may extend along top surface 304 and/or second housing portion 320, as a portion of the first or second housing portion itself or a component extending along an outer surface of the first or second housing portion, with conductive surfaces of the electrodes exposed through polymer enclosure 310.

Figure 10:
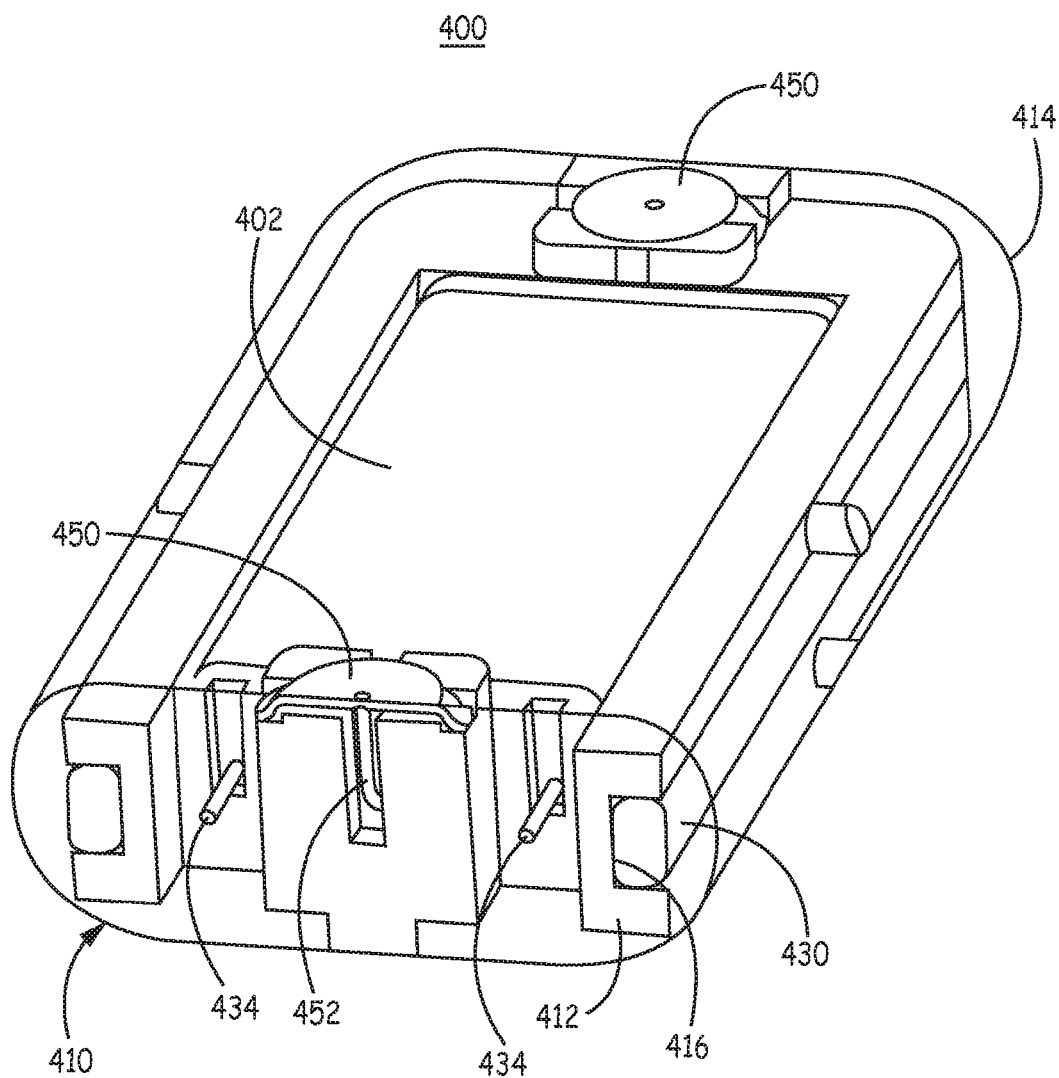
FIG. 10 is a perspective view of an exemplary overmolded housing including a flanged housing portion.

FIG. 10 is a perspective view of an overmolded housing 400 including a first housing portion 402. First housing portion 402 is sealed to a second housing portion along a seal area (not seen in the view of FIG. 10). The seal area may exist between an outwardly extending flange of portion 402 and a portion of the second housing portion overlapping the flange as described in conjunction with FIG. 9. Alternatively, the first housing portion 402 does not include a flange, and the first and second housing portions may be sealed along any other mating surfaces. A first shot 412 of a polymer enclosure 410 is molded over the first housing portion 402 and the second housing portion (not seen in FIG. 10) to embed and surround a mated, sealed interface between the first and second housing portions. The first shot 412 circumscribes the housing 400 along its lateral sides and ends, along a sealed joint between the first and second housing portions.

The first shot 412 includes a groove 416 for retaining a conductive coil 430. The first shot 412 may serve as a mandrel for winding the coil. Feedthrough pins 434 extend outward from housing portion 402 and are electrically coupled to the coil 430 to provide electrical connection to electronics housed within housing portion 402. Coil 430 may be used for charging a rechargeable battery housed within portion 402 or may be used to inductively power the circuitry within housing 400 for delivering neurostimulation therapy in an externally powered system. The conductive coil can be made from any suitable material. Applicants have found that use of niobium for the coil (in this and the other exemplary embodiments herein) allows the coil to be used as both the power transfer and telemetry (or communications) coils while at the same time allowing a biocompatible and biostable coil design. Additionally, since niobium is biocompatible, the niobium coil can optionally be located outside of the hermetic seal of the housing.

Electrodes 450 are shown positioned along opposing ends of the first housing portion 402. Electrodes 450 are electrically coupled to feedthrough pins 452 to provide electrical connection to electronics housed within first housing portion 402. The first shot 412 may be molded with the necessary grooves, recesses and other features to enable assembly of the electrodes 450 along the ends of housing portion 402 and electrical coupling of the electrodes 450 to the feedthrough pins 452 after molding of the first shot. Alternatively, the electrodes 450 may already be connected to feedthrough pins 452 and held within a mold during overmolding of the first shot 412 such that the feedthrough pins 452 and bottom portions of electrodes 450 become embedded in the first shot 412.

A second shot 414 is molded over and surrounds the first shot 412, coil 430, the first housing portion 402 and the second housing portion and seal area. The second shot surrounds and embeds the connections between feedthrough pins 434 and coil 430 and feedthrough pins 452 and electrode 450 (if assembled after forming first shot 412) to reduce the likelihood of corrosion due to body fluids. A top surface of each of electrodes 450 is exposed through the second shot 414 to provide anode and cathode electrode surfaces for delivering an electrical stimulation therapy.

In this way, the first shot 412 provides a protective barrier over the sealed area of housing portion 402 to a second housing portion, both to provide a smooth surface over housing edges and to protect the seal along the housing portions and the circuitry within the housing. The first shot 412 additionally provides grooves, recesses or other features for stably positioning and retaining electrical components existing outside of the sealed housing portion 402, e.g. electrodes 450, coil 430 and connections to feedthrough pins 434 and 452. The second shot 414 encloses all of the electrical components and connections located external to the housing portion 402, with the exception of the active surfaces of the electrodes 450.

The first shot 412 and the second shot 414 may be formed from an injectable or moldable thermoset or thermoplastic polymer including, but not limited to, liquid crystal polymer, polysulfone, polyurethane, polyether ether ketone, epoxy, diamond like carbon, silicone, PURSIL® silicone polyether urethane available from DSM, Berkeley, Calif., USA, or any combination thereof.

By positioning coil 430 outside of the housing portion 402, more efficient energy transfer can be achieved between an external primary coil and secondary coil 430. In alternative embodiments, a telemetry antenna could be positioned along a groove formed in first shot 412, in addition to or instead of the coil 430.

Figure 11:
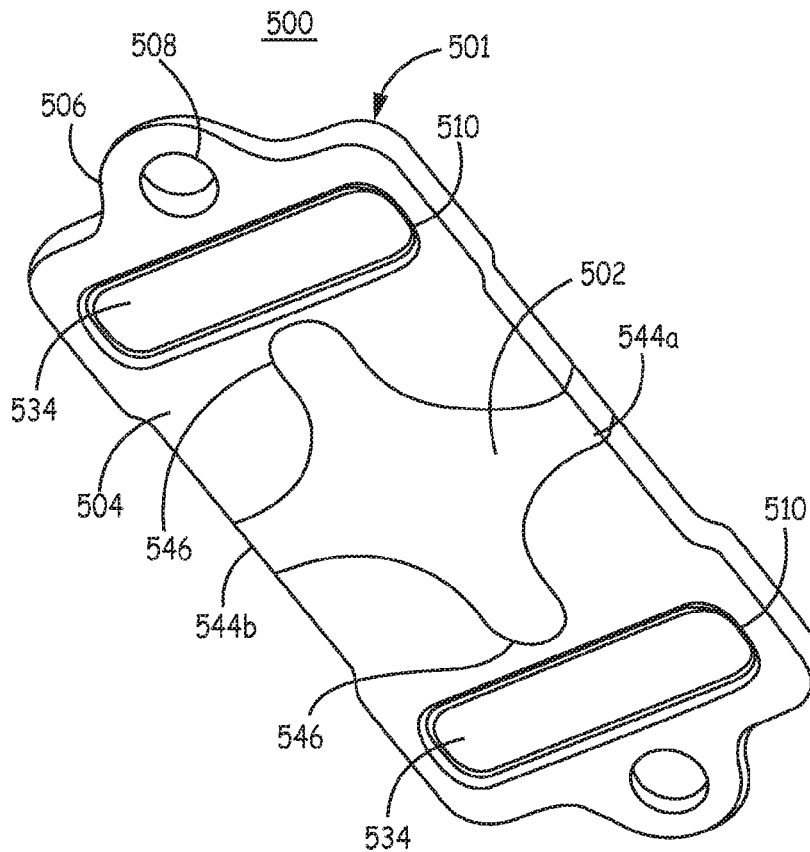
FIG. 11 is a perspective view of an exemplary IMD including an overmolded housing according to an alternative embodiment.

FIG. 11 is a perspective view of an IMD 500 including an overmolded housing according to an alternative embodiment. IMD 500 includes electrodes 510 exposed through an overmolded housing 501. Housing 501 includes a support member 502 having portions 544a, 544b, and 546 described further below and an overmold member 504. Housing 501 may be formed from a biostable or biocompatible polymer having a low moisture absorption rate such as liquid crystal polymer (LCP), polyether ether ketone (PEEK), or polysulfone. Operating electrode surfaces 534 of electrodes 510 are exposed through the overmolded member 504. The overmolded member 504 may include one or more protruding members 506 and/or one or more inner surfaces 508 defining a suture guide or other fixation members or guides to promote stable positioning of IMD 500 at an implant site.

Figure 12:
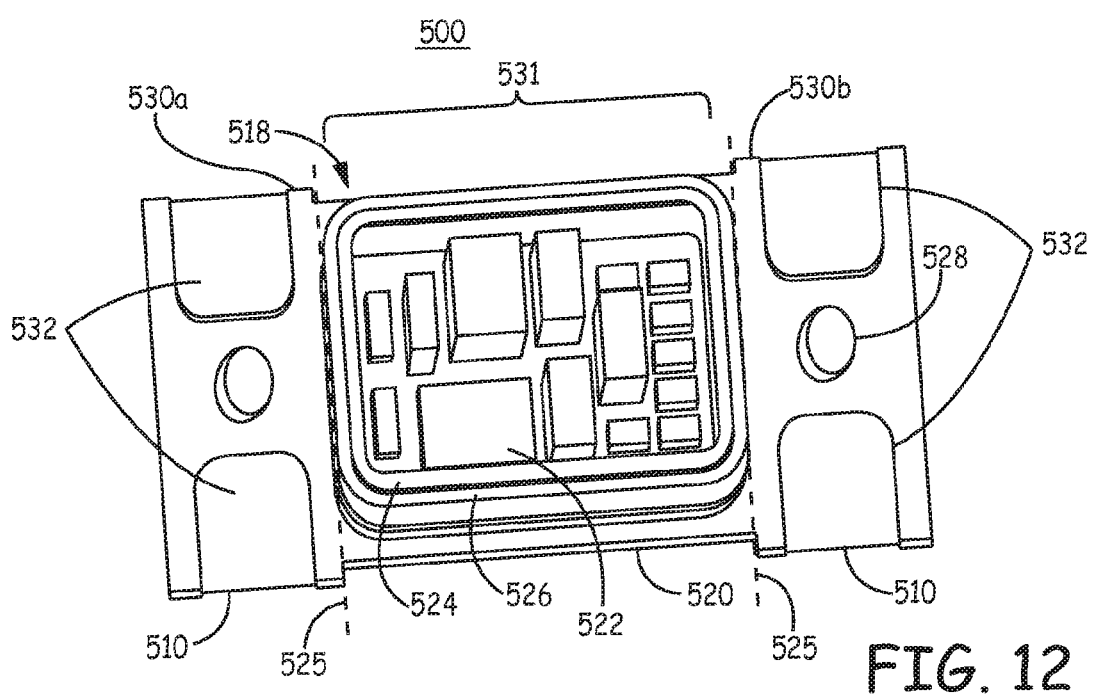
FIG. 12 is a perspective view of a flexible circuit included in the IMD shown in FIG. 11 according to one exemplary embodiment.

FIG. 12 is a perspective view of a flexible circuit 518 included in IMD 500 shown in FIG. 11 according to one embodiment. Electronic circuitry 522 is mounted on a flexible substrate 520. The flexible substrate 520 could include thin copper or thin titanium conductors laminated within a polyimide or thin liquid crystal polymer. Electrical interfaces may be coated with a highly conformable coating such as paralene, epoxy, or liquid silicone rubber to protect against corrosion.

A mandrel 524 surrounds circuitry 522 and supports a conductive coil 526. In the embodiment shown, IMD 500 is an externally powered device including a secondary coil 526 for receiving inductively transmitted power from an external device (outside the patient's body) for powering circuitry 522 after implantation. An electrical feedthrough (not shown in the view of FIG. 12) connects coil 526 to circuitry 522 through a via formed in or beneath mandrel 524. Alternatively coil 526 is coupled to circuitry 522 by a conductive via extending within flexible substrate 520.

Electrodes 520 may be electrically coupled to circuitry 522 by conductive vias extending through substrate 520. Each of electrodes 510 are shown as an elongated conductive strip that is wrapped around flexible substrate 520, having anchoring portions 532 that are folded or wrapped around substrate 520 to hold the operating electrode surface 534 (FIG. 11) in a stable position on the opposing side of substrate 522. Flexible substrate 520 includes a middle portion 531 extending between opposing first and second ends with a first tab 530a and a second tab 530b extending from each of the opposing first and second ends of the middle portion 531. Tabs 530a and 530b are provided as extensions of flexible substrate 520 for carrying electrodes 510 directly on the substrate 520. Accordingly, electrodes 510 can be electrically coupled directly to circuitry 522 using conductive traces extending through flexible substrate and do not require a feedthrough extending through a sealed housing. Protective potting material 528 may be used to cover and protect an interconnect between a via and electrodes 510. Electrodes 510 become stably mounted on flexible substrate 520 and within overmold member 504, with operating electrode surfaces 534 exposed through overmold member 504.

In one embodiment, the housing 501 shown in FIG. 11 is a flexible polymer material to enable folding of electrodes 510 underneath and behind circuitry 522, along fold lines 525, such that electrodes 510 lay against the outer surface of the housing 501 opposite circuitry 522 (i.e. beneath circuitry 522 in the view shown in FIG. 12). This foldability of flexible circuit 518 provides a relatively smaller, injectable device during implantation of IMD 500, allowing a smaller incision for the implant procedure. Upon release from an injection tool, the tabs 530a and 530b will extend to the normally open position as shown in FIG. 12, thereby positioning the active electrode surfaces 534 in contact with body tissue at a targeted therapy site.

Upon unfolding to a normally open position after release from an implant tool, IMD 500 is restored to a relatively flatter profile at an implant location, allowing the IMD 500 to lay generally flat beneath the skin, muscle or other tissue layer. For example, the IMD 500 may be injected in a compact folded position superficially to a deep fascia tissue layer superior to the flexor retinaculum, against or in close proximity to a targeted tibial nerve extending beneath the deep fascia. When unfolded, the electrodes are positioned adjacent the nerve superficially to the deep fascia providing a relatively large electrode surface area integrated in the IMD 500 itself in close proximity to the target site.

Figure 13:
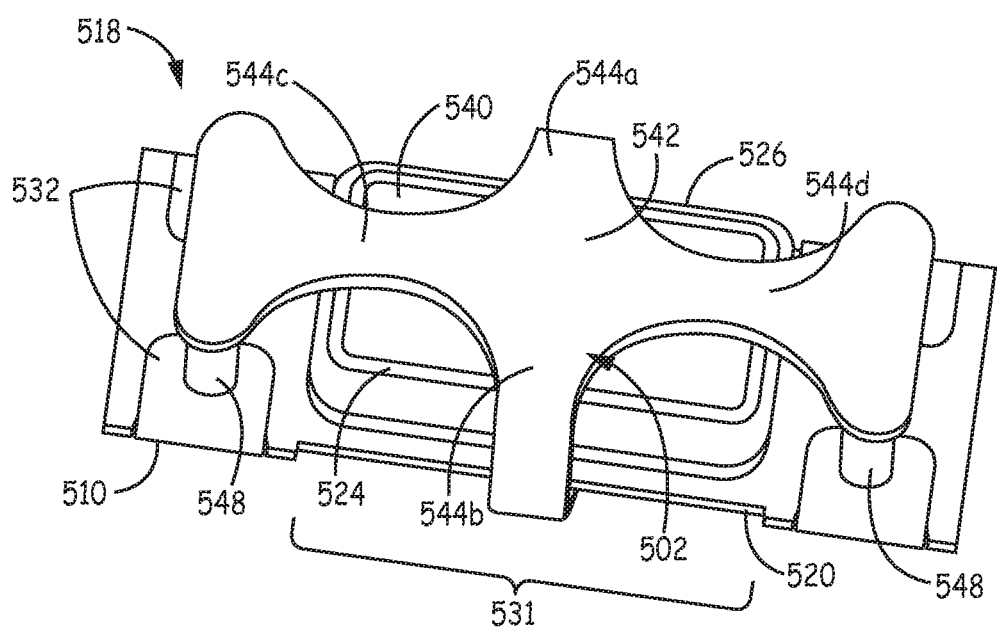
FIG. 13 is a perspective view of electronic circuitry and a support member of the IMD shown in FIG. 11.

FIG. 13 is a perspective view of the flexible circuit 518 and support member 502 of IMD 500 shown in FIG. 11. A mandrel 524 serves as a dam for an electronics sealing member 540 that seals and covers electronic circuitry 522 (shown in FIG. 12), protecting circuitry 522 from corrosive body fluids. In various embodiments, electronics sealing member 540 may be an epoxy potting material, an injection molded thermoplastic, a thermally set coating, a wafer scale silicone cover, or localized thermally melted glass. Corrosion protection of the electronic circuitry 522 (not seen in FIG. 13) is provided by localizing the electronics sealing member 540, which can be assembled within mandrel 524 to seal off and enclose circuitry 522, using a highly automated manufacturing process.

In some embodiments, sealing member 540 is injected into mandrel 524 and cured. In other embodiments, sealing member 540 is a pre-molded component that is set into place and bonded to mandrel 524 using an adhesive material or a thermal, chemical or other joining method to fixedly attach sealing member 540 to mandrel 524 and/or circuitry 522 and/or substrate 520 within the boundaries of mandrel 524. Circuitry 522 becomes potted or embedded in sealing member 540 in some embodiments, and in other embodiments circuitry 522 is sealed beneath member 540.

Support member 502 may be a pre-molded component bonded to the flexible substrate 520 or a first shot overmolded component. The "hour glass" shape of support member 502 may provide passive fixation of IMD 500 when overmold member 504 is provided as a non-rigid material. When the overmold member 504 is cured over support member 502, shrinkage of overmold member 504 may expose portions of support member 502, as shown in FIG. 11. Exposed portions of support member 502, which may include varying widths and/or protruding members, may act to passively fix IMD 500 at a desired implant site.

Support member 502 may be formed from a thermoplastic or other rigid polymer material to provide mechanical support to IMD 500. In one embodiment, support member 502 includes studs 548 that press against electrode anchoring portions 532 to provide additional anchoring of electrode 510 to substrate 520. In this case, IMD 500 is not a foldable device as described above.

In other embodiments, support member 502 is a flexible or stretchable material enabling folding of flexible circuit 518 along the fold lines shown in FIG. 12. In still other embodiments, support member 502 is a rigid support member but does not extend beyond middle portion 531 of substrate 520.

Support member 502 includes a middle portion 542 and multiple arms 544a, 544b, 544c, and 544d extending outward from middle portion 542. Opposing arms 544a and 544b extend around substrate 520 in one embodiment and may extend entirely around substrate 520, as shown in FIG. 11, such that arms 544a and 544b meet and form a continuous supportive ring around substrate 520. Arms 544a and 544b may include lateral extensions 546 as shown in FIG. 11 for added support of flexible circuit 518.

Returning to the view of FIG. 13, opposing arms 544c and 544d may include studs 548 for stably anchoring electrodes 510 and provide mechanical support along a long axis of flexible circuit 518. As shown in FIG. 11, an overmold member 504 is overmolded to surround flexible circuit 518 and may surround support member 502 or leave portions of support member 502 exposed as described above. In this way, the electrodes 510 (with the exception of the active surfaces 534) and a secondary coil 526 for an externally powered or a rechargeable device may be sealed and stably mounted within the housing 501 but external to sealed circuitry 522. Circuitry 522 is protected by sealing member 540 and housing 501 while the electrical components carried by flexible circuit 518 external to mandrel 524 are protected and stably housed within housing 501.

Figure 14:
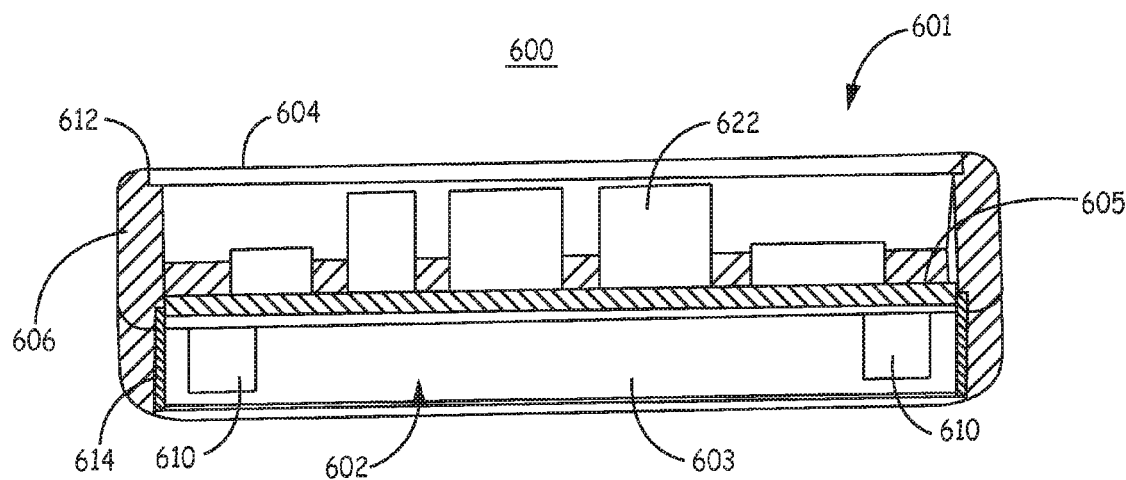
FIG. 14 is cut-away perspective view of an exemplary IMD having a housing including at least one side formed from a cofire ceramic circuit substrate.

FIG. 14 is cut-away perspective view of an IMD 600 having a housing 601 including at least one side formed from a cofired ceramic circuit substrate 602. IMD electronic circuitry 622 enclosed within housing 601 is mounted on a top surface 605 of cofire substrate 602, which becomes an inner surface of housing 601. Cofire substrate 602, and other cofire substrates described herein, may include vias within the substrate that connect through substrate layers, and can provide access for electrical connectivity to inner surface 605 and outer surface 603.

One or more electrodes 610 extend along a bottom surface 603 of cofire substrate 602, which becomes an outer surface of housing 601. Electrodes 610 may be integrated directly in the substrate 602 at the time of firing, providing an electrically active surface exposed along bottom surface 603 for delivering neurostimulation or sensing electrophysiological signals. Alternatively, electrodes 610 may be bonded or metalized onto cofire substrate 602 in a separate step after firing. Electrodes 610 are electrically coupled to electronic circuitry 622 via conductive traces extending within substrate 602. In this way, electrodes 610 are integrated in the housing 601, having one outer surface 603 formed by the cofired substrate 602.

Cofire substrate 602 is bonded at joint 614 to a ferrule 606, which may be a ferrule formed from stainless steel, titanium, niobium, tantalum, platinum, iridium, MP35N, or any combination or alloys thereof. Joint 614 may be a brazed joint (e.g. a gold braze), a diffusion bonded joint, or a joint formed by local heating of glass. Joint 614 may be covered by an epoxy, thermoset, or thermoplastic resin, or medical adhesive to further seal and protect against corrosion.

In some embodiments, a pre-formed glass member may be locally heated to seal joint 614. However, a pre-formed glass member may be costly or challenging to manufacture in the small size required in a miniaturized IMD used for minimally invasive medical applications. As such, in other embodiments, a glass paste formed from a biocompatible glass compound, e.g. a lead-free glass compound, is locally heated to form joint 614. A glass paste applied at joint 614 may be a mixture of a finely ground glass compound mixed with isopropyl alcohol and optionally a binder. The glass paste may be applied to joint 614 using a syringe or screen printing. The glass paste is locally heated to melt the glass to thereby form a glass sealed joint. The heating may be performed in two stages wherein a first intermediate temperature, e.g. approximately 300 degrees C., is applied to off gas non-glass components of the paste and a second relatively higher temperature, e.g. 800 degrees C., is applied to melt the glass and form the glass seal at joint 614.

In various housing embodiments described herein, this type of glass seal may be used between a metal and non-metal component to form a sealed joint along an IMD housing, including joints between housing portions, between a ferrule and a housing portion, and along an electrical feedthrough such as between a feedthrough pin and a ceramic filter or insulating sleeve.

Ferrule 606 is joined to a housing lid 604, which may be a titanium lid or other metal or metal alloy listed previously herein, enabling welding of the ferrule and lid at joint 612 to seal housing 601. In some embodiments, ferrule 606 and lid 604 are laser welded to form a hermetically sealed joint 612. Ferrule 606 and lid 604 are shown as two separate components, which may be machined components, sealed at joint 612. Ferrule 606 may have varying internal diameters as shown to form grooves or ridges to mate with and receive lid 604 as well as cofire substrate 602. In alternative embodiments, ferrule 606 and lid 604 are formed as a single stamped or formed component that is sealed to cofire substrate 602 along joint 614.

In one embodiment, cofire substrate 602 includes a non-silicate based glass to form a biostable low-temperature cofire ceramic. Low-temperature cofire ceramics generally include a lead-based silicate glass. The lead-based glass systems can contain significant levels of alkali oxides within the glassy phase. The alkali oxides pose challenges due to the ready migration of ions in the glass and phase separation and/or crystallization that can occur as aluminum oxide dissolves during the firing process, limiting the firing profiles that may be achieved.

Substrate 602, however, may be based on a non-silicate glass, such as CaBA1-12 ($20CaO.20MgO.20Al_2O_3.40B_2O_3$) or LaBor-4 ($20CaO.20MgO.15Al_2O_3.5La_2O_3.10SiO_2.30B_2O_3$) glass, which can be processed below 1,000 degrees C. to produce cofire assemblies. The low temperature cofire ceramic enables for direct firing of passive components such as resistors into the substrate 602. The non-silicate glass-based co-fire ceramic has a relatively higher aluminum oxide solubility than the silicate glass based systems so that dissolution of alumina during firing is not expected to result in phase separation or crystallization. The non-silicate glass based cofire substrate will be free of alkali oxides providing greater biostability of housing 601 compared to lead-based silicate cofire systems and will be voltage bias stable. Gold-based interconnects may be used in forming electrical connections between electrical components of or coupled to circuitry 622. Elimination of PbO from the low temperature silicate phase improves biocompatibility of the assembly for implantable medical use.

In implementing a low temperature non-silicate glass based cofire ceramic for producing substrate 602, various electrical components can be incorporated in the substrate 602. Electrical components that may be fired within substrate 602 may include but are not limited to feedthrough filters, a telemetry communication antenna, communication circuitry, and electrodes 610. By incorporating components within substrate 602, space otherwise taken up by these components on the upper surface 605 (inner surface of housing 601) is freed up for other circuit components and/or the overall IMD size may be reduced.

Figure 15A:
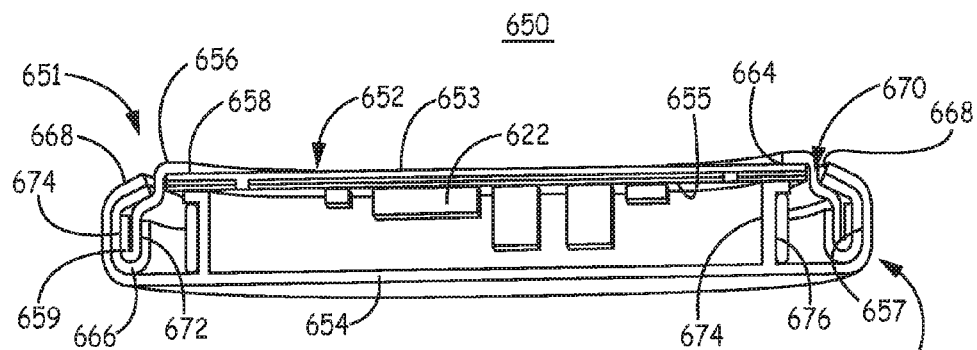
FIG. 15A is a cut-away perspective view of an IMD according to an alternative exemplary embodiment including a housing with at least one side being a surface of a cofire ceramic substrate.

FIG. 15A is a cut-away perspective view of an IMD 650 according to an alternative embodiment including a housing 651 with at least one side being a surface of a cofire ceramic substrate. Housing 651 includes cofire ceramic substrate 652, ferrule 656 and lid 654. Ferrule 656 and lid 654 are titanium in one embodiment but may be formed or stamped from other metals or metal alloys listed herein. Ferrule 656 includes an outer edge 658 and an inner edge 659. Inner edge 659 may optionally be formed as a U-shaped bend in ferrule 656 in one embodiment, as shown in FIG. 15A, to provide greater strength along edge 659 during a crimping process as will be described below.

Ferrule 656 is sealingly joined to the substrate outer surface 653 (which is an outer surface of housing 601) at joint 664 near and along ferrule outer edge 658. Joint 664 may be formed using a gold braze, diffusion bonding or localized heating of glass, as described previously. One or more electrodes may be incorporated in substrate 652 and exposed along outer surface 653 as described above. Cofire substrate 652 may include a non-silicate glass as described above. Electronic circuitry 622 is mounted on inner surface 655 of substrate 652. Components of circuitry 622 or components coupled to circuitry 622 may be incorporated in cofire substrate 652 at the time of firing.

Lid 654 is mechanically coupled and sealed to ferrule 656 by a crimp joint 662. Crimp joint 662 includes a polymer seal 666 that is positioned between ferrule 656, along inner ferrule edge 659 prior to forming crimp joint 662. Lid 654 is provided with an outer dimension greater than the outer dimension of substrate 652 to provide a length and width required to bend outer edge 668 of lid 654 around ferrule inner edge 659 and toward outer surface 653 of cofire substrate 652. In some embodiments, lid 654 or a portion thereof may function as an electrode and be electrically coupled to substrate 652 and electronics 622.

Ferrule 656 includes varying outer diameters to form a face or ridge for interfacing with crimped lid 654. For example, as shown in FIG. 15A, lid outer edge 668 is crimped against an outwardly extending lateral ridge 670 of ferrule 656. Ridge 670 is formed by a bend in ferrule 656 intermediate ferrule ends 658 and 659. Polymer seal 666 extends along both an inwardly facing surface 672 of ferrule 656, i.e. facing toward the interior of housing 651, and an outwardly facing surface 674 of ferrule 656, i.e. facing toward the exterior of housing 651, such that polymer seal 666 becomes compressed between ferrule outwardly facing surface 674, including lateral ridge 670, and the inner surface 657 of lid 654. Vertical compression between ridge 670 and lid 654 provides a reliable seal to reduce the likelihood of ingress of bodily fluids, thereby protecting internal circuitry 622 from corrosion. Polymer seal 666 may be formed of silicone rubber, synthetic rubbers such as polyisobutylene or thermoplastic's such as PEEK, polypropylene, polyphenylene sulfide, polysulfone, polyvinylidene chloride, polytetraflouroethylene, polyethylene or laminated moisture barrier films or coatings. Crimp joint 662 encompassing polymer seal 666 thereby provides a sealed internal cavity defined by substrate 652, lid 654 and ferrule 656 within which electronic circuitry 622 is housed.

In the embodiment shown in FIG. 15A, a mandrel 674 is coupled to an inner surface 655 of substrate 652 and supports a secondary coil 676 when IMD 650 is a rechargeable or externally powered device. Coil 676 is retained within a cavity defined by mandrel 674, lid 654 and ferrule 656 and protected from body fluids by crimp seal 662.

Figure 15B:
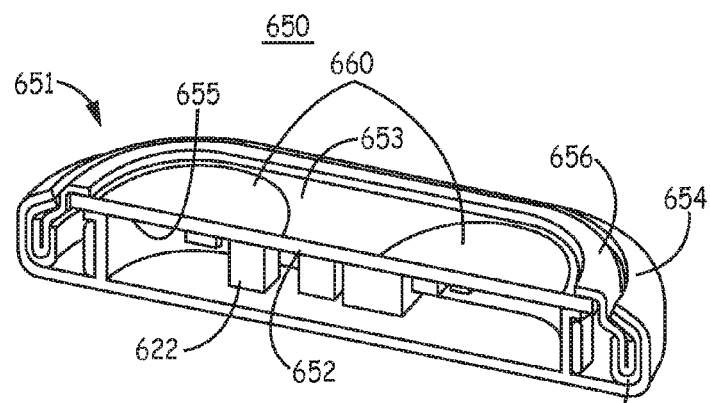
FIG. 15B is a cut-away perspective view of the IMD shown in FIG. 15A according to one embodiment.

FIG. 15B is a cut-away perspective view of the IMD 650 shown in FIG. 15A according to one embodiment. The outer surface of housing 651 includes outer surface 653 of cofire substrate 652. Electrodes 660 are positioned along outer surface 653 and electrically coupled to internal electronic circuitry 622 by vias extending through the layers of cofire substrate 652. Electrodes 660 may be platinum or platinum iridium, for example, and may be formed along surface 653 during the cofire process or assembled on surface 653 after firing. Electrodes 660 may be coated to enhance the electrode surface, e.g. using a fractal TiN coating. Other high surface area coatings like IrOx among others could be used as a coating of the active, exposed surface of the Pt or PtIr electrode. If electrodes 660 are assembled on outer surface 653 of substrate 652, the electrodes 660 may include titanium, tantalum, stainless steel or any alloy thereof but will most likely yield better performance if coated with a high surface area coating as described above. By incorporating electrodes 660 along cofire substrate outer surface 653, no feedthrough connections are required through housing 651 to connect electrodes 660 to circuitry 622. In this embodiment, two electrodes 660 are shown along surface 653, however it is recognized that one or more electrodes may be positioned along surface 653.

Figure 16:
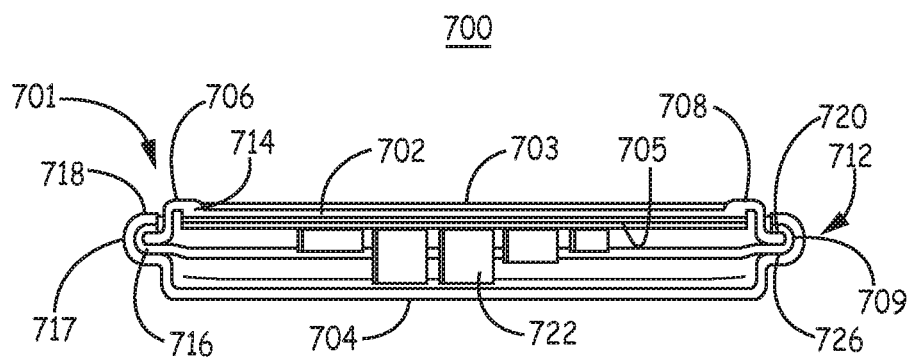
FIG. 16 is a cut-away perspective view of an alternative exemplary embodiment of an IMD including a housing having a lid sealed to a ferrule by a crimp joint.

FIG. 16 is a cut-away perspective view of an alternative embodiment of an IMD 700 including a housing 701 having a lid 704 sealed to a ferrule 706 by a crimp joint 712. In this embodiment, ferrule 706 is shown having a generally "S" or "Z" shaped cross-section such that a first edge 708 extends over the outer surface 703 of cofire substrate 702 and a second edge 709 extends laterally outward, forming a flange 720. First edge 708 is bonded to cofire substrate at joint 714, e.g. using a metallic braze, localized heated glass as described above, a diffusion bond, or other appropriate method for bonding ferrule 706 to substrate 702.

Lid 704 includes a C-shaped bend 717 near outer edge 718 that is crimped around ferrule flange 720. Accordingly, in this embodiment, lid 704 is crimped around an edge 709 of ferrule 706 as compared to the embodiment shown in FIG. 15A where lid 654 is crimped around a ridge 670 formed intermediate the first and second edges 658 and 659 of ferrule 656. A polymer seal 716 is wrapped around ferrule edge 709 such that polymer seal 716 becomes compressed between an inner surface 726 of lid 704 and ferrule flange 720, sealing an interior chamber of housing 701, defined by cofire substrate 702, lid 704 and ferrule 706. Though not shown in FIG. 16, it is recognized that a secondary coil for enabling recharging of a battery or for transmission of power from an external source for powering circuitry 722 may be supported by a mandrel included within housing 702.

Figure 17:
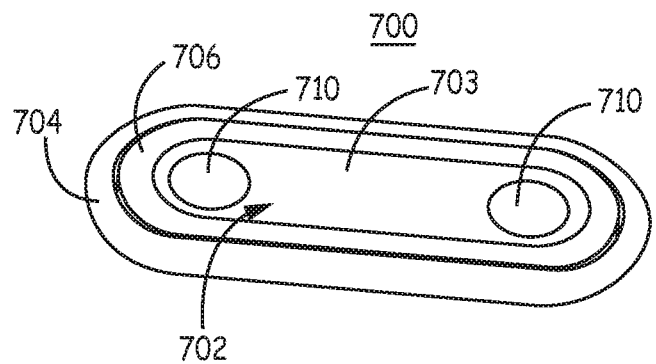
FIG. 17 is a top perspective view of the IMD shown in FIG. 16.

Outer surface 703 of substrate 702 forms an exterior surface of housing 701. Substrate 702 may include electrically conductive vias extending through layers of substrate 702 to form connection points along external surface 703 for electrically coupling electrodes positioned along external surface 703 to circuitry 722 mounted on internal surface 705 of substrate 702. As shown in the top perspective view of FIG. 17, one or more electrodes 710 may be formed along an external surface 703 of cofire substrate 702, eliminating the need for providing insulated feedthroughs as separate components extending through housing 701 (formed by substrate 702, lid 704 and ferrule 706) for coupling electrodes to internal circuitry 722.

Figure 18:
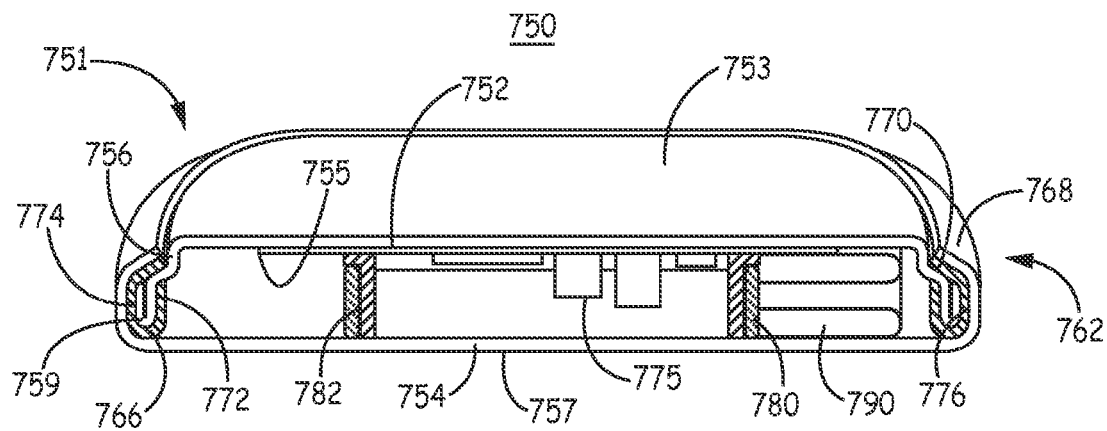
FIG. 18 is a cut-away perspective view of an exemplary IMD having a sealed housing including a crimp joint between a lid and a cofire ceramic substrate.

FIG. 18 is a cut-away perspective view of an IMD 750 having a sealed housing 751 including a crimp joint 762 between a lid 754 and a housing portion 752. In the embodiment shown in FIG. 15A, a ferrule 656 bonded to cofire substrate 652 provides the inner structure against which the outer edge 668 of lid 654 is crimped. In the embodiment of FIG. 18, housing portion 752 forms both a top outer surface 753 of housing 751 and a side wall 756 which provides the inner structure against which an outer edge 768 of lid 754 is crimped. Housing portion 752 is generally "U" shaped having a top outer surface 753 and a side wall 756. Sidewall 756 may be provided with varying outer diameters to provide a lateral surface, e.g. a ridge 770, or other interfacing surface against which lid 754 is crimped.

Housing portion 752 includes an edge 759 around which a polymer seal 766 extends. As shown in FIG. 18, side wall 756 may include varying wall thicknesses separating inner side 772 and outer side 774 of side wall 756 so as to provide added strength along edge 759 or other points along side wall 756 during a crimping procedure. The polymer seal 766 is compressed between an inner surface 776 of lid 754 and outer side 774 of side wall 756. Polymer seal 766 may extend further along side wall inner surface 772. In this way, the housing portion 752 forms a top outer surface 753 of housing 751; the lid 754 forms an opposing or bottom outer surface 757 of housing 751, and a crimp joint 762 between housing portion 752 and lid 754 forms a sealed peripheral side wall of housing 751, separating top outer surface 753 and bottom outer surface 757 of housing 751.

Circuitry 775 is housed within the enclosure defined by housing portion 752 and lid 754 and is protected from bodily fluid ingress by the sealed crimp joint 762. In some embodiments, a mandrel 782 may be mounted on an inner surface 755 to support a secondary coil 780 included for inductive power transmission when IMD 750 is an externally powered or rechargeable device. Electrical feedthroughs may extend through or beneath mandrel 782 to provide electrical connection between coil 780 and circuitry 775.

As described below in conjunction with FIG. 19B, bottom surface 757 of lid 754, or a portion thereof, may be configured as an electrode in some embodiments. An electrical connection between bottom surface 757 and electronic circuit 775 may be implemented as a serpentine flextape interconnect 790 that provides electrical connection between lid 754 and housing portion 752. The flextape interconnect 790, being flexible and extendable, enables electrical coupling between lid 754 and housing portion 752 to be performed before assembling lid 754 onto housing portion 752. For example flextape interconnect 790 may be electrically coupled by welding, staking, or crimping other connection means to a via connection point on circuitry 775 and welded, crimped or staked to a connection point along lid 754 prior to assembling lid 764 onto housing portion 752.

Figure 19A:
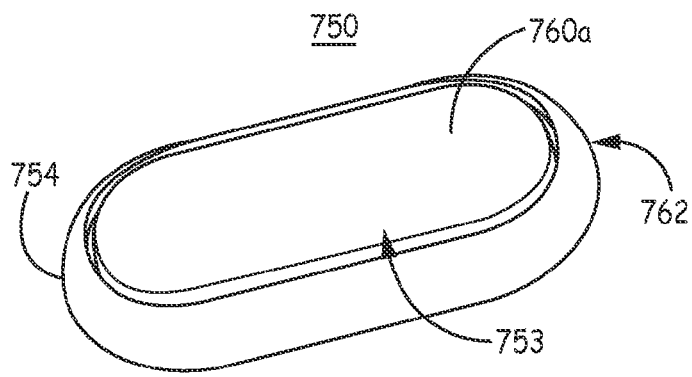
FIGS. 19A and 19B are top and bottom perspective views, respectively, of the IMD shown in FIG. 18.
Figure 19B:
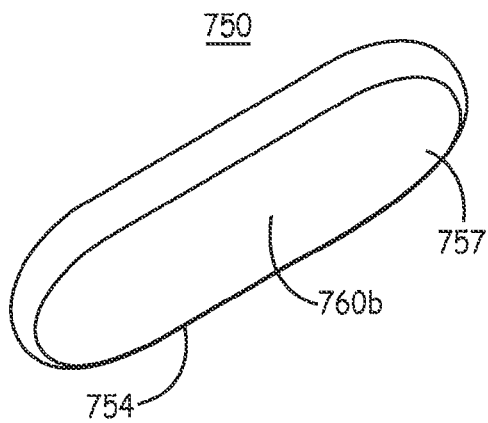

FIGS. 19A and 19B are top and bottom perspective views, respectively, of IMD 750 shown in FIG. 18. In one embodiment, the top surface 753 of housing portion 752 is a conductive surface and forms an electrode 760a. The opposing bottom surface 757 of housing 751 defined by lid 754 functions as a second electrode 760b. Electrode 760b is electrically coupled to circuitry 775. In one embodiment, electrode 760b is coupled to circuitry 775 by a conductive wire extending from lid 754 directly to circuitry 775. In another embodiment, lid 754 is electrically coupled to a via connection point on side wall inner surface 772. An electrode 760b may be formed along a portion of bottom surface 757 by providing an insulating coating over other portions of bottom surface 757 in some embodiments. It is further contemplated that one or more electrodes may be formed along surface 757 by providing multiple uninsulated portions separated by insulated portions of surface 757, each having insulated electrical connections to circuitry 775.

Figure 20:
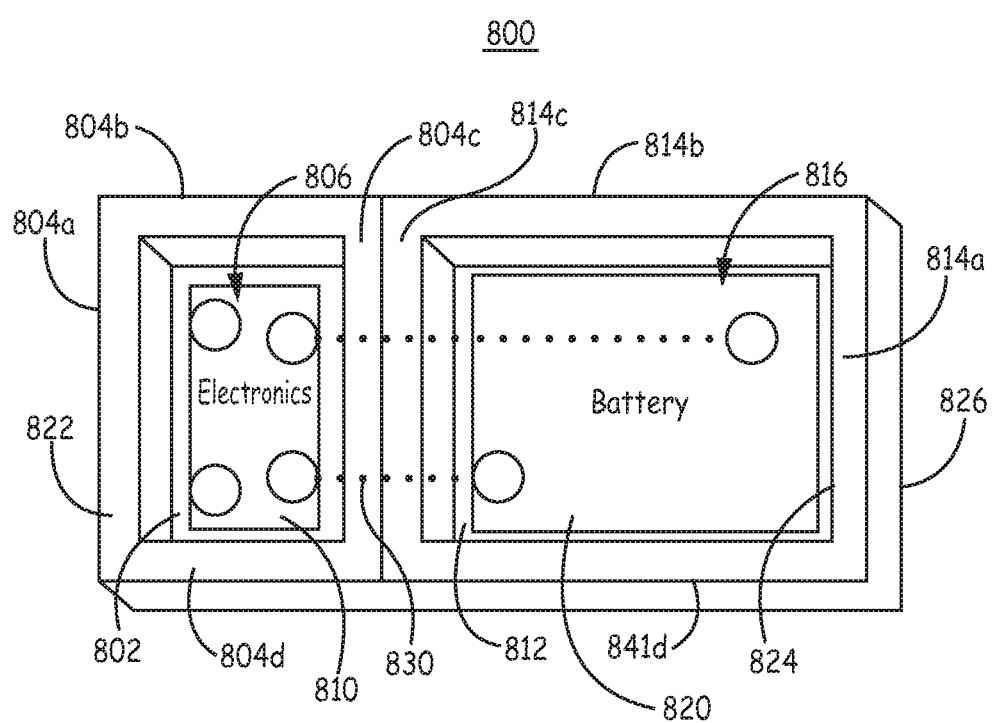
FIG. 20 is a top perspective view of a cofire ceramic substrate according to one exemplary embodiment.

FIG. 20 is a top perspective view of a cofire ceramic substrate 800 according to one embodiment. A cofire ceramic substrate 800 included in the various embodiments described herein may include multiple cavities defined by a base of the substrate and surrounding side walls. As shown in FIG. 20, a base 802 and surrounding side walls 804a through 804d define a cavity 806. Electronic circuitry 810 may be assembled along base 802, and electrical components may be formed in the cofired layers of base 802 and/or side walls 804a through 804d.

A second cavity 816 is shown formed by base 812 surrounded by side walls 814a through 814d. A battery 820 is shown housed within cavity 816. Battery components may be assembled in cavity 816 during a manufacturing process, or battery 820 may be pre-assembled and installed in cavity 816. Battery 820 may be electrically coupled to electronic circuitry 810 by conductive vias 830 extending through bases 802 and 812 and/or side walls 804c and 814c.

In some embodiments, cofire ceramic substrate 800 is formed as a single component with multiple cavities separated by inner side walls 804c and 814c. In other words, bases 802 and 812 may form a continuous base of a substrate having peripheral outer walls 804a,b,d and 814a,b,d forming a continuous outer peripheral side wall. One or more interior walls 804c, 814c extending between inner surfaces of the peripheral outer walls 804a,b,d and 814a,b,d separates two or more interior cavities 806, 816.

In other embodiments, multiple cofire ceramic substrates each having a base and a side wall extending upward from the base along at least one side of the base may be formed and assembled together to form a cofire ceramic substrate assembly defining multiple cavities. For example, base 802 may be surrounded on all four sides by side walls 804a,b,c,d and base 812 may be surrounded on three sides by side walls 814a,b,d and joined to sidewall 804c to form a cofire ceramic substrate 800 having two cavities. In FIG. 20, cavities 806 and 816 are shown separated by a double layer (side walls 804c and 814c) however in other embodiments cavities may be separated by a single layered side wall extending between peripheral sidewalls to define separate interior cavities.

Side walls 804a, 804b, 804d and 814a, 814b and 814d define peripheral or outer side walls of cofire substrate 800, having an outer surface 826 and inner surface 824 separated by a side wall thickness. The outer side walls 804a,b,d and 814a,b,d may have a varying outer diameter to provide ridges, grooves, flanges, or other features for mating with a lid, a ferrule, an inductive coil, or providing a crimp joint surface as described in various embodiments above. Additionally or alternatively, outer side walls 804a,b,d and 814a,b,d may have varying wall thickness to provide differing strength characteristics and/or differing outer diameters and/or differing inner diameters.

A top surface 822 of side walls 804a-d and 814a-d may be mechanically coupled and sealed to a ferrule or a lid to form a sealed housing according to the various techniques described herein. In some embodiments, a secondary coil may be wrapped around outer surface 826 for use in recharging battery 820 or for powering circuitry 810 (if battery 820 is not present or in combination with battery 820). As described above, one or more electrodes may be formed along the outer surface of bases 802 and 812.

In some embodiments, a sealing material (not shown in FIG. 18) may seal cavities 806 and 816. Side walls 804a-d and 814a-d may form dams for a potting material injected into cavities 806 and 816. In various embodiments, an epoxy potting material, an injection molded thermoplastic, a thermally set coating, a wafer scale silicone cover, or localized thermally melted glass may be used to seal cavities 806 and 816.

In other embodiments, a metallic lid of titanium, niobium, tantalum, platinum, iridium, MP35N, stainless steel, and/or alloys thereof may alternatively be sealed to the top surface 822 using a gold braze, glass sealing or diffusion bonding technology to make the cavities hermetic. A lid could be a single lid component sealed with a directed energy source to top surface 822, e.g. using a braze, diffusion bond, or glass seal. Alternatively, a frame may be positioned around and furnace sealed to the outer peripheral walls 804a,b,d and 814a,b,d prior to assembly of the electronic 810 and battery 820 within cavities 806 and 816. A lid may then be laser welded to the frame or joined using any of the other techniques described herein to seal cavities 806 and 816 after assembly of electronic circuitry 810 and battery 820 within cavities 806 and 816.

Figure 21:
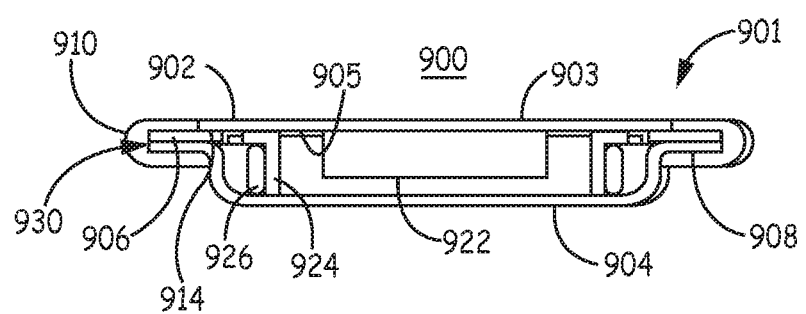
FIG. 21 is a cut-away side perspective view of an exemplary IMD according to yet another embodiment.

FIG. 21 is a cut-away side perspective view of an IMD 900 according to yet another embodiment. IMD 900 includes a housing 901 enclosing internal electronic circuitry 922 and optionally a secondary coil 926 supported by a mandrel 924. Housing 901 includes a cofire ceramic substrate 902, a flanged ferrule 906 and a flanged lid 904. Ferrule 906 is sealed at joint 914 to an inner surface 905 of cofire substrate 902, e.g. using a metallic braze, locally heated glass, diffusion bonding or other appropriate bonding methods. Flanged ferrule 906 is coupled to lid flange 908, e.g. using roller welding, laser welding or other joining methods. The joint 930 formed between ferrule 906 and lid flange 908, as well as the outer edges of ferrule 906 and lid ferrule 908, are enclosed by a polymer enclosure 910. In an alternative embodiment, a flanged ferrule 906 may be sealed to top outer surface 903 of cofire substrate 902 and include a flange extending laterally outward to mate with lid flange 908.

Polymer enclosure 910 may be a preformed or overmolded component formed from a biocompatible thermoset or thermoplastic material, such as but not limited to silicone rubber, polyurethane LCP or polysulfone or other polymer enclosure or overmold materials previously listed. Polymer enclosure 910 provides a smooth edge around flange 908 for reducing patient discomfort that may otherwise be caused by flange 908 and for protecting the joint 930 between flange 908 and ferrule 906.

Figure 22:
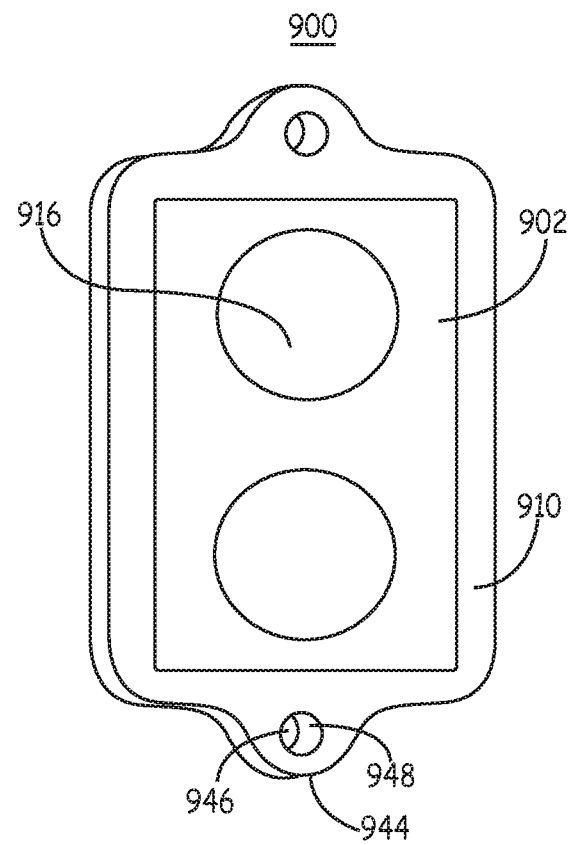
FIG. 22 is a top perspective view of the IMD shown in FIG. 21.

As shown in the top perspective view of IMD 900 in FIG. 22, polymer enclosure 910 may include features for facilitating implantation and/or fixation of IMD 910. In one example, polymer enclosure 910 includes a protruding suture tab 944, which may include a preformed suture hole 946 defined by an inner surface 948 of tab 944. In other embodiments, tab 944 may be a solid portion of enclosure 910 which a suture may be advanced through using a needle or wrapped around to facilitate anchoring of IMD 900. In various embodiments, enclosure 910 may include a tab, protrusion, ring, groove, channel or other feature that facilitates securing of a suture or other fixation device to IMD 900 for anchoring IMD 900 at a desired implant site. Additionally or alternatively, enclosure 910 may include one or more barbs, tines, hooks, or other protruding features to promote fixation of device 900. As described previously, one or more electrodes 916 may be incorporated along a top outer surface 903 of cofire substrate 902 and be electrically coupled to electronic circuitry 922 by vias extending through layers of substrate 902.

Figure 23:
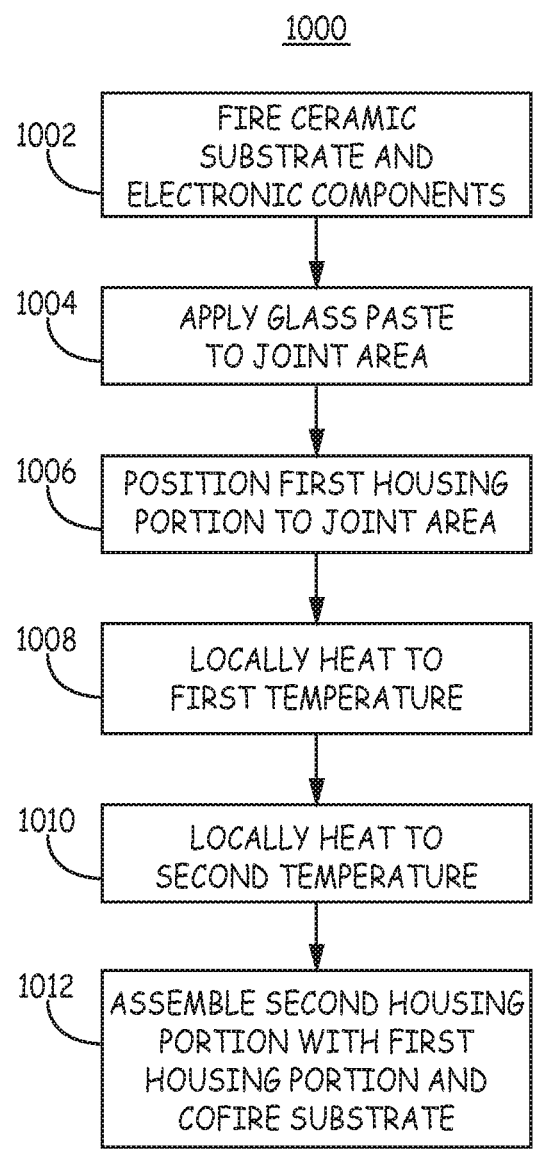
FIG. 23 is a flow chart of an exemplary method of manufacturing an IMD housing.

FIG. 23 is a flow chart of a method 1000 of manufacturing an IMD housing. At block 1002, a low temperature cofire ceramic substrate is fired, with IMD electronic components incorporated in the layers of the ceramic substrate in some embodiments. At blocks 1004 through 1010, the cofire ceramic substrate is sealed to a first housing portion. The first housing portion may be a metallic ferrule or may be a metallic lid. In the process shown by flow chart 1000, the seal is formed at a joint between the cofire ceramic substrate and the first housing portion using a glass paste at block 1004.

A glass paste is applied to a joint area, for example by a syringe or screen printing as described previously herein. The first housing portion is positioned along the cofire substrate to mate with the substrate along the joint area at block 1006. The joint area is locally heated to a first temperature to off-gas paste byproducts at block 1008 and to a second temperature higher than the first temperature to melt the glass and seal the cofire substrate to the first housing portion at block 1010.

In alternative embodiments, a braze joint or a diffusion bonded joint may be formed between the cofire ceramic substrate and a first housing portion. In still other embodiments, a sealed joint is formed by crimping the first housing portion around the ceramic substrate and an intervening polymer seal.

At block 1012, a second housing portion may be assembled with the cofire substrate and the first housing portion. For example, a housing lid may be welded or crimped to a ferrule sealed to the cofire substrate. Additionally or alternatively, a polymer enclosure or overmold member may be applied along a portion of the cofire substrate and first housing portion (and a lid if present), e.g. along sealed joints.

Figure 24:
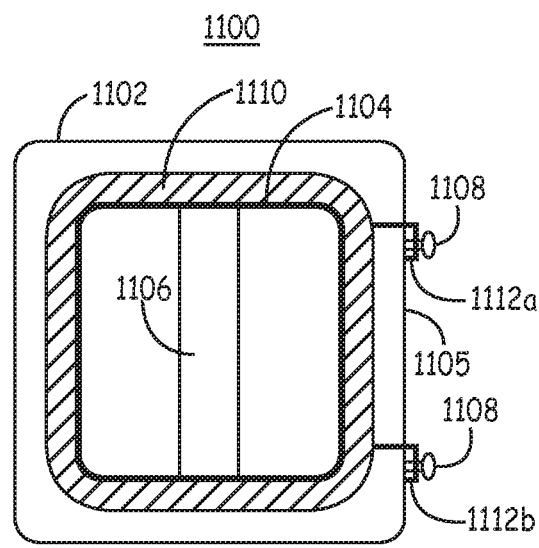
FIG. 24 is a top plan view of an exemplary inductive coil wound around a polymer bobbin or mandrel.

FIG. 24 is a top plan view of an inductive coil 1110 wound around a polymer bobbin or mandrel 1100. The mandrel 1100 includes a laterally extending horizontal portion 1102 intersecting with vertical wall 1104. Coil 1110 is wrapped around vertical wall 1104. Mandrel 1100 may include one or more cross beams 1106 extending between opposing sides of vertical wall 1104. Cross beam 1106 may provide structural support to mandrel 1100 and may facilitate pick and place manufacturing assembly methods.

First and second coil ends 1112a and 1112b extend along horizontal portion 1102 to a respective wire guide 1108 which guides threading of wire coil ends 1112a and 1112b around an outer edge 1105 of mandrel 1100 to extend along a bottom, selectively metalized surface of mandrel 1100. Guides 1108 are optional and in other embodiments wire coil ends 1112a and 1112b may extend directly around outer edge 1105 or may be threaded through an aperture formed in horizontal portion 1102.

Figure 25:
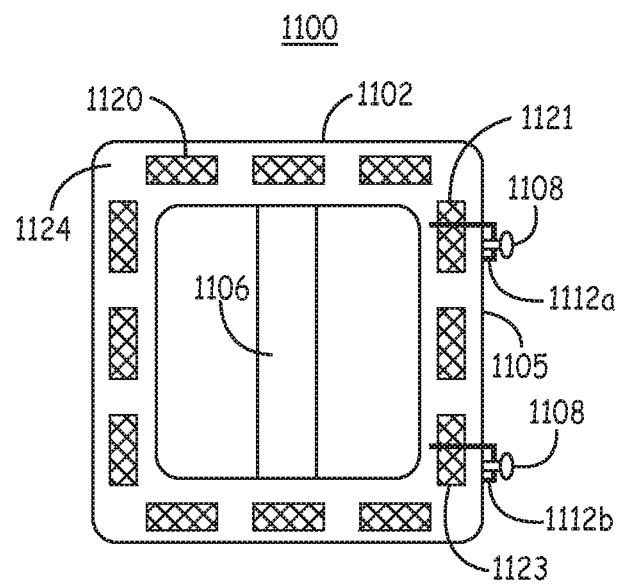
FIG. 25 is a bottom plan view of the mandrel of FIG. 24.

FIG. 25 is a bottom plan view of mandrel 1100. Mandrel 1100 includes metallic pads 1120 along bottom surface 1124 of horizontal portion 1102. Metallic pads may be selectively plated along bottom surface 1124 using a nickel and gold alloy in one embodiment though other metals or metal alloys may be used. Metallic pads 1120 may be selectively metalized along bottom surface 1124 after performing a laser activation of polymer bottom surface 1124. A VECTRA® molded interconnect device having selective metallization of a thermoplastic injection molded part that could be adapted to function as a mandrel 1100 can be supplied by Ticona Inc., Florence, Ky., USA.

Coil ends 1112*a,b* extend around outer edge 1105 and guides 1108 if present to extend over coil interconnect pads 1121 and 1123, respectively. Bottom surface 1124 may be coupled to connection pads of an associated ceramic substrate by soldering metallic pads 1120, 1121 and 1123 to the connection pads. The coil ends 1112*a,b*, extending along interconnect pads 1121 and 1123 will be electrically coupled to a conductive via when pads 1121 and 1123 are soldered to associated connection pads along a ceramic substrate. Insulation around wire coil ends 1112*a,b* will be melted away during a soldering process enabling insulation removal, electrical coupling and mechanical coupling of mandrel 1100 and coil 1110 assembly to a ceramic substrate or printed circuit board in a single manufacturing step.

Interconnect pads 1121 and 1123 may include copper plating for electrical coupling to coil ends 1112*a,b*, respectively. Interconnect pads 1121 and 1123 may include a groove for receiving coil ends 1112*a,b*.

Figure 26:
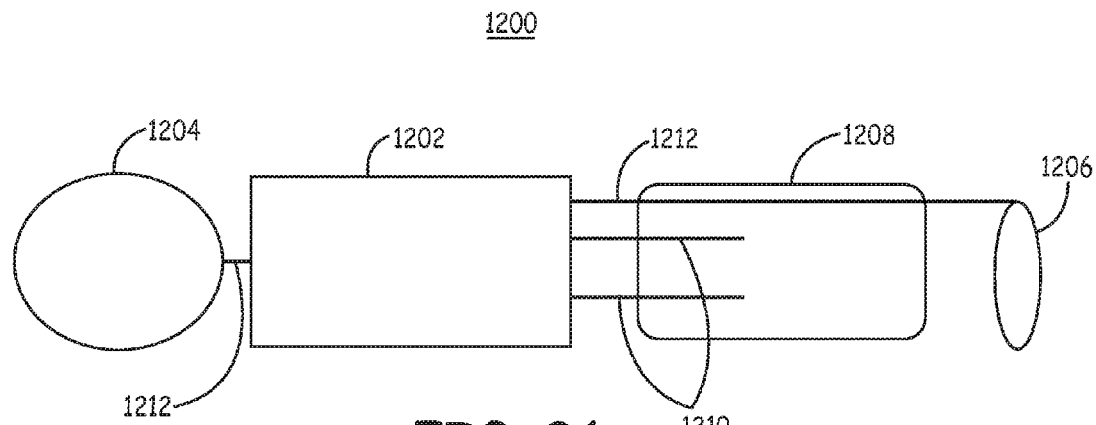
FIG. 26 is schematic diagram of an exemplary formed housing assembly.

FIG. 26 is schematic, exploded diagram of a formed housing assembly 1200. A formed housing 1202 may be a single drawn, elongated tube of titanium or a titanium alloy (or other metal or metal alloy previously listed herein). The elongated tubular housing 1202 may be utilized as a coil mandrel for an externally powered or rechargeable IMD. Coil 1208 may be wound around elongated housing 1202 along either a long axis or a short axis of the elongated housing 1202. Coil 1208 may be overmolded with a polymer coating or encasement and is electrically coupled to electronic circuitry enclosed within elongated tubular housing 1202 by insulated electrical feedthroughs 1210. Feedthroughs 1210 may be assembled along a single end of housing 1202 or one feedthrough 1210 may be assembled at each end of the housing 1210.

End cap electrode assemblies 1204 and 1206 seal opposing ends of the elongated tubular housing 1202. In one example, a ferrule ring is welded to the housing 1202 and an electrode is carried by the ferrule but electrically insulated therefrom. In other embodiments, end cap assemblies 1204 and 1206 may include a ferrule ring formed of a ceramic sealed to housing 1202 by a braze, diffusion bond, or glass seal or a polymer molded over ends of housing 1202 in a one-shot or two-shot process. Electrodes carried by assemblies 1204 and 1206 are electrically coupled to IMD circuitry within housing 1202 by insulated electrical feedthroughs 1212. End cap assemblies 1204 and 1206 may be provided as molded or formed components comprising grooves, notches, or other features to accommodate coil 1208 and feedthrough connection points.

Figure 27:
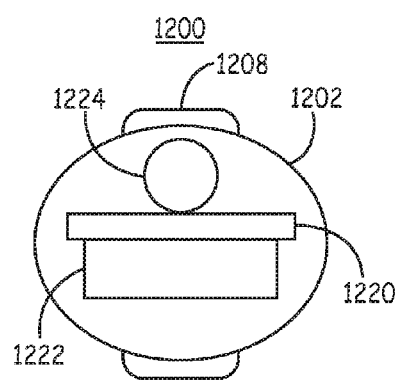
FIG. 27 is an end sectional view of the housing assembly of FIG. 26.

FIG. 27 is an end sectional view of housing assembly 1200 shown in FIG. 26. The housing 1202 may further enclose a ferrite or high permeability rod 1224 to improve inductive coupling of energy from a primary coil located outside the patient's body to coil 1208 wrapped around housing 1202. Coil 1208 is shown wrapped around a long axis of housing 1202 in FIG. 27 but could alternatively be wrapped around a short axis of housing 1202 with ferrite rod 1224 positioned appropriately relative to coil 1208. Ferrite rod 1224 may be mounted along one side of a circuit substrate 1220 and IMD electronic circuitry 1222 may be mounted on the opposing side of substrate 1220.

Figure 28:
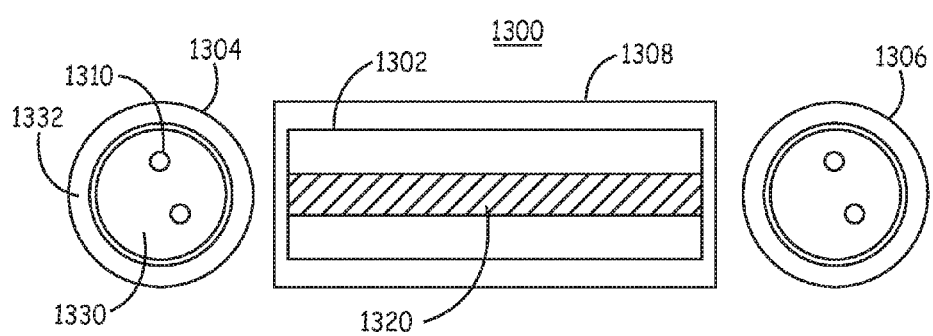
FIG. 28 is a schematic diagram of an IMD housing assembly according to an alternative exemplary embodiment.

FIG. 28 is a schematic diagram of an IMD housing assembly 1300 according to an alternative embodiment. Housing assembly 1300 includes a tubular elongated ceramic housing 1302 and end caps 1304, 1306 sealing opposing ends of housing 1302. Housing 1302, shown from a side sectional view, encloses a ferrite rod 1320 and IMD circuitry. Electrodes (not seen in the sectional view of housing 1302) may be plated directly onto an exterior surface of ceramic housing 1302 and coupled to electronic circuitry enclosed by housing 1302 by conductive vias extending through ceramic layers. IMD electronic circuitry can be mounted directly onto the interior surface of housing 1302. Using the ceramic housing 1302 as an electrode substrate and circuit substrate enables miniaturization of the IMD.

The housing 1302 may be formed as a single tube having a circular or elliptical cross-section, though other cross sections are possible, with end caps 1304 and 1306 brazed, diffusion bonded, or glass sealed onto the opposing ends of the ceramic housing 1302. The end caps 1304 and 1306 may include a weld ring 1332 that is sealed to housing 1302 and seam welded to a center cap 1330. End caps 1304 and/or 1306 may include feedthrough apertures 1310 for enabling electrical connection of ends of coil 1308 to insulated electrical feedthroughs to thereby couple coil 1308 to circuitry enclosed by housing 1302.

The housing 1302 serves as a mandrel for coil 1308 wrapped around housing 1302. Coil 1308 may be overmolded or coated with a protective polymer layer. Ferrite rod 1320 improves inductive coupling of energy transfer to coil 1308 from an external primary coil and energy transfer does not get restricted by the eddy current heat that might occur in housings formed from conductive materials such as titanium. In alternative embodiments, coil 1308 may be positioned inside housing 1302, around a bobbin or mandrel, with a ferrite rod 1320 core.

Figure 29:
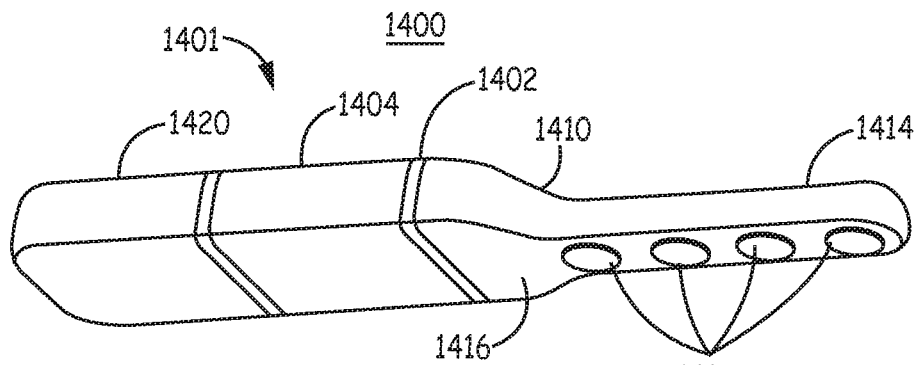
FIG. 29 is a perspective view of a minimally invasive IMD for delivering neurostimulation therapy according to an alternative exemplary embodiment.

FIG. 29 is a perspective view of a minimally invasive IMD 1400 for delivering neurostimulation therapy according to an alternative embodiment. IMD 1400 includes a housing 1401 including a metallic shroud 1404 supported by a metal injection molded chassis 1402 for enclosing IMD internal electronic circuitry. Shroud 1404 may be a thin metallic sheet of titanium or a titanium alloy mounted on and encircling chassis 1402. For example a high resistivity titanium alloy including aluminum and vanadium, e.g. 6% aluminum and 4% vanadium, may be used to form metallic shroud 1404.

IMD 1400 further includes a "pig-tail" lead 1410 coupled to one end of housing 1401. Pigtail lead 1410 includes a proximal connector portion 1416 and a flattened distal paddle portion 1414 carrying multiple electrodes 1412 adapted to be positioned along a targeted nerve, e.g. the tibial nerve, for delivering a neurostimulation therapy. Distal paddle portion 1414 may be adapted for positioning over a deep tissue fascia layer, superior to the flexor retinaculum, or beneath the fascia layer and/or retinaculum, with electrodes 1412 selectable for delivering stimulation pulses to the tibial nerve. Pigtail lead 1410 may be non-removable from housing 1401 in some embodiments such that IMD 1400 including housing 1401 and lead 1410 is provided as a single manufactured assembly. In other embodiments, pigtail lead 1410 may be connectable/disconnectable from housing 1401.

End cap 1420 may be provided as a battery cavity coupled to an opposing end of chassis 1402 for retaining a rechargeable battery cell or a primary cell. End cap 1420 may enclose an air core or ferrite core coil when IMD 1400 is externally powered or a rechargeable device. Alternatively, end cap 1420 may be a generally flattened end cap that does not add substantial volume to IMD 1400 and all electronics are enclosed within foil 1404 and chassis 1402. In other examples, an end cap electrode assembly may be assembled onto one or both ends of chassis 1402.

Figure 30:
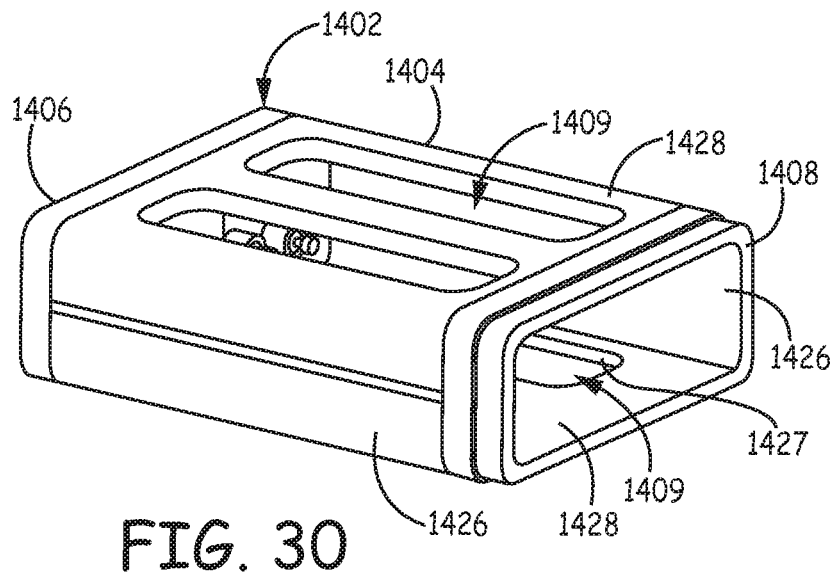
FIG. 30 is a perspective view of a metal injection molded chassis and metallic shroud included in an exemplary IMD housing.

With continued reference to FIG. 29, FIG. 30 is a perspective view of the metal injection molded chassis 1402 for supporting metallic shroud 1404 of housing 1401. Chassis 1402 includes minor opposing side walls 1426 and major opposing side walls 1428 extending between opposing ends 1406 and 1408. Shroud 1404 is wrapped entirely around side walls 1426 and 1428 to wholly circumscribe chassis 1402 along side walls 1426 and 1428, defining a tubular structure having an interior cavity for enclosing IMD circuitry. Varying outer diameters of side walls 1426 and 1428 near ends 1406 and 1408 as shown in FIG. 30 facilitate alignment and guidance of shroud 1404 when being wrapped around and mounted on chassis 1402. Shroud 1404 is mechanically coupled to chassis 1402, e.g. laser welded in place.

The varying outer diameters of chassis 1402 may additionally provide mating interfaces for assembly with end cap 1420 and pigtail lead 1410. The molded metallic chassis 1402 provides optimal weld joint interfaces for mechanically coupling and sealing of lead 1410 and end cap 1420 to form a sealed housing 1401. Other features may be molded into chassis 1402 such as a battery cavity, coil bobbin or mandrel, component retention features, screw bosses, notches, struts or other structural features that provide support, eliminate separate components, reduce overall IMD size, and/or promote ease of assembly of IMD 1400.

One or more of side walls 1406 and 1408 may include one or more apertures 1427 defining openings 1409. By maximizing openings 1409 along side walls 1406 and 1408 while still providing adequate support for shroud 1404, housing 1401 minimizes attenuation of magnetic or RF coupling to a secondary coil enclosed by housing 1401. The use of an increased resistivity shroud 1404 further improves inductive coupling.

Figure 31:
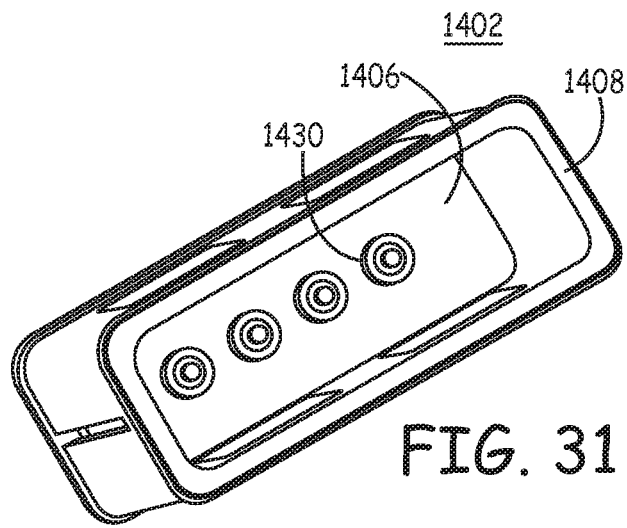
FIG. 31 is an end perspective view of an exemplary metal injection molded chassis.

FIG. 31 is an end perspective view of metal injection molded chassis 1402. One end 1408 may be an open end for coupling to end cap 1420 defining a battery cavity. Opposing end 1406 may be a closed end including multiple feedthroughs 1430 for electrically coupling electrodes 1412 (shown in FIG. 29) to IMD circuitry enclosed within chassis 1402 and shroud 1404. The feedthroughs 1430 may include glass seals formed by local heating of a glass paste as described previously.

Figure 32:
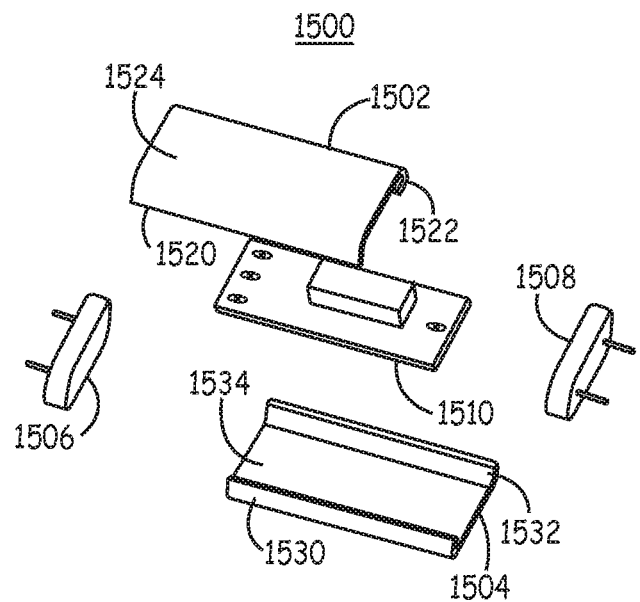
FIG. 32 is an exploded view of an exemplary IMD including machined housing portions.

FIG. 32 is an exploded view of an IMD 1500 including machined housing portions. IMD 1500 includes a first housing portion 1502 and a second housing portion 1504 which are machined portions each having opposing minor sidewalls 1520, 1522 and 1530, 1532 separated by a major side wall 1524 and 1534, respectively. First and second housing portions 1502 and 1504 are assembled together by mating minor side walls 1520, 1522 and 1530, 1532 and attaching machined feedthrough end cap assemblies 1506 and 1508. An IMD circuit board 1510 is enclosed within first and second housing portions 1502 and 1504 during assembly.

Figure 33:
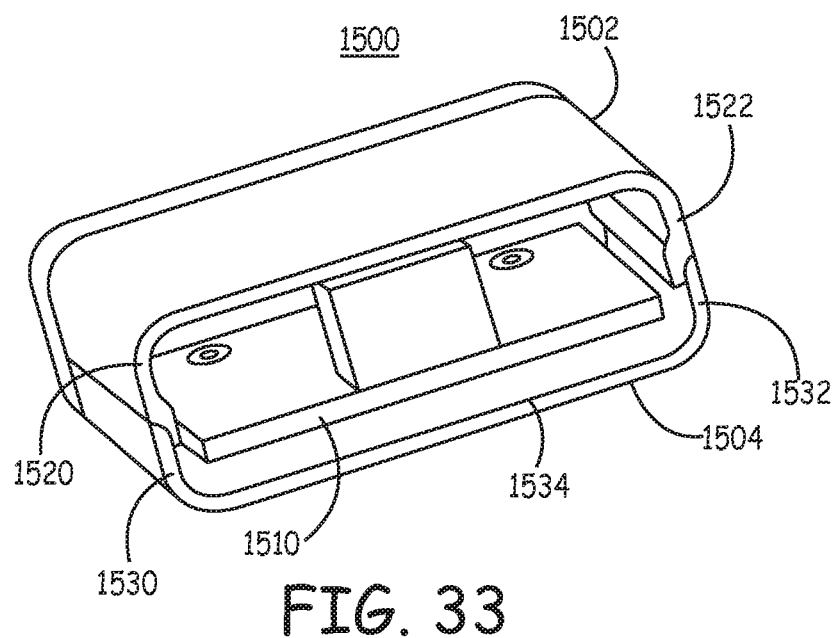
FIG. 33 is a perspective sectional view of the IMD of FIG. 32.

FIG. 33 is a perspective sectional view of IMD 1500 of FIG. 32. Minor side walls 1520 and 1522 of first housing portion 1502 are shown having an underlapping edge for interfacing with minor side walls 1530 and 1532 of second housing portion 1504. This machined feature enables laser seam welds to be performed along the under- and over-lapping portions of respective side walls 1520, 1522 and 1530, 1532 to provide a sealed interior cavity for housing circuit board 1510

Figure 34:
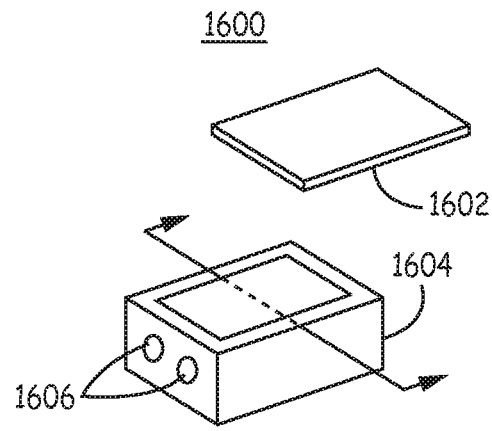
FIG. 34 is a perspective view of an exemplary IMD housing including a first housing portion that is a machined or metal injection molded housing portion and a second housing portion that is a stamped housing portion.

FIG. 34 is a perspective view of an IMD housing 1600 including a first housing portion 1604 that is a machined or metal injection molded housing portion and a second housing portion that is a stamped housing portion 1602. Stamped housing portion 1602 is sealed to first housing portion 1604 to provide a sealed cavity enclosing IMD circuitry. First housing porting may include one or more feedthrough apertures 1606 along any sidewall for electrically coupling IMD components external to housing 1600.

Figure 35:
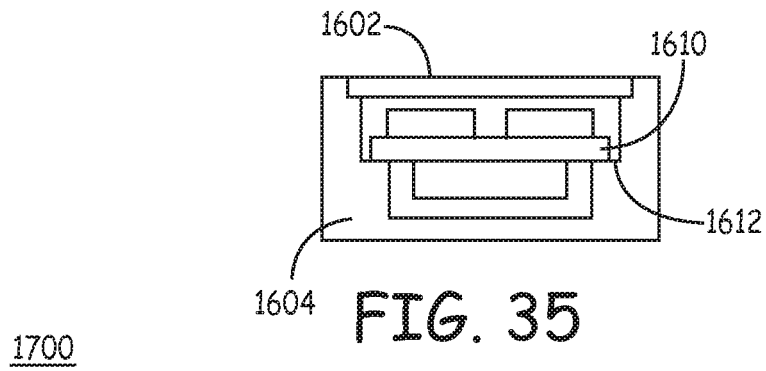
FIG. 35 is an end sectional view of the IMD housing of FIG. 34.

FIG. 35 is an end sectional view of IMD housing 1600 of FIG. 34. First housing portion 1604 may varying include interior diameters to facilitate assembly of internal IMD components and stamped housing portion 1602. For example, first housing portion 1604 may be machined or molded to include a shelf 1612 for assembling a circuit board 1610 within housing 1600. Circuit board 1610 held along shelf 1612 allows electronic circuit components to be positioned along both top and bottom surfaces of circuit board 1610.

Figure 36:
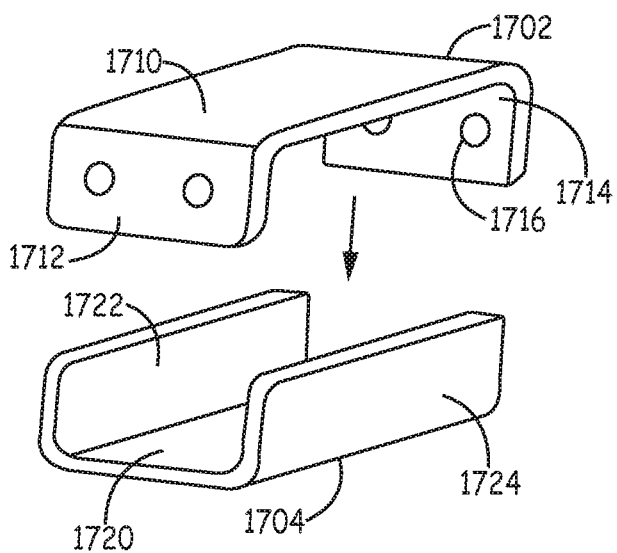
FIG. 36 is an exploded view of an alternative exemplary IMD housing including a first housing portion that is a machined or metal injection molded housing portion mated with a second housing portion, which is a stamped housing portion.

FIG. 36 is an exploded view of an alternative IMD housing 1700 including a first housing portion 1702 that is a machined or metal injection molded housing portion mated with a second housing portion 1704, which is a stamped housing portion. First housing portion is machined or molded to include a major side wall 1710 extending between opposing end walls 1712 and 1714. End walls 1712 and 1714 may include one or more feedthrough apertures 1716 for facilitating electrical connection to components enclosed within housing 1700.

Second housing portion is stamped to include a major side wall 1720 and opposing minor side walls 1722 and 1724. Housing 1700 is assembled by aligning and mating first and second housing portions such that end walls 1712, 1714, major side walls 1710 and 1720, and minor side walls 1722 and 1724 define an interior cavity for enclosing IMD circuitry. First and second housing portions may be seam welded along mating sides.

Accordingly, in various embodiments described herein a minimally invasive IMD housing may include a machined metal housing portion, a metal injection molded portion, a stamped metal housing portion, a cofire ceramic housing portion or any combination thereof.

Figure 37:
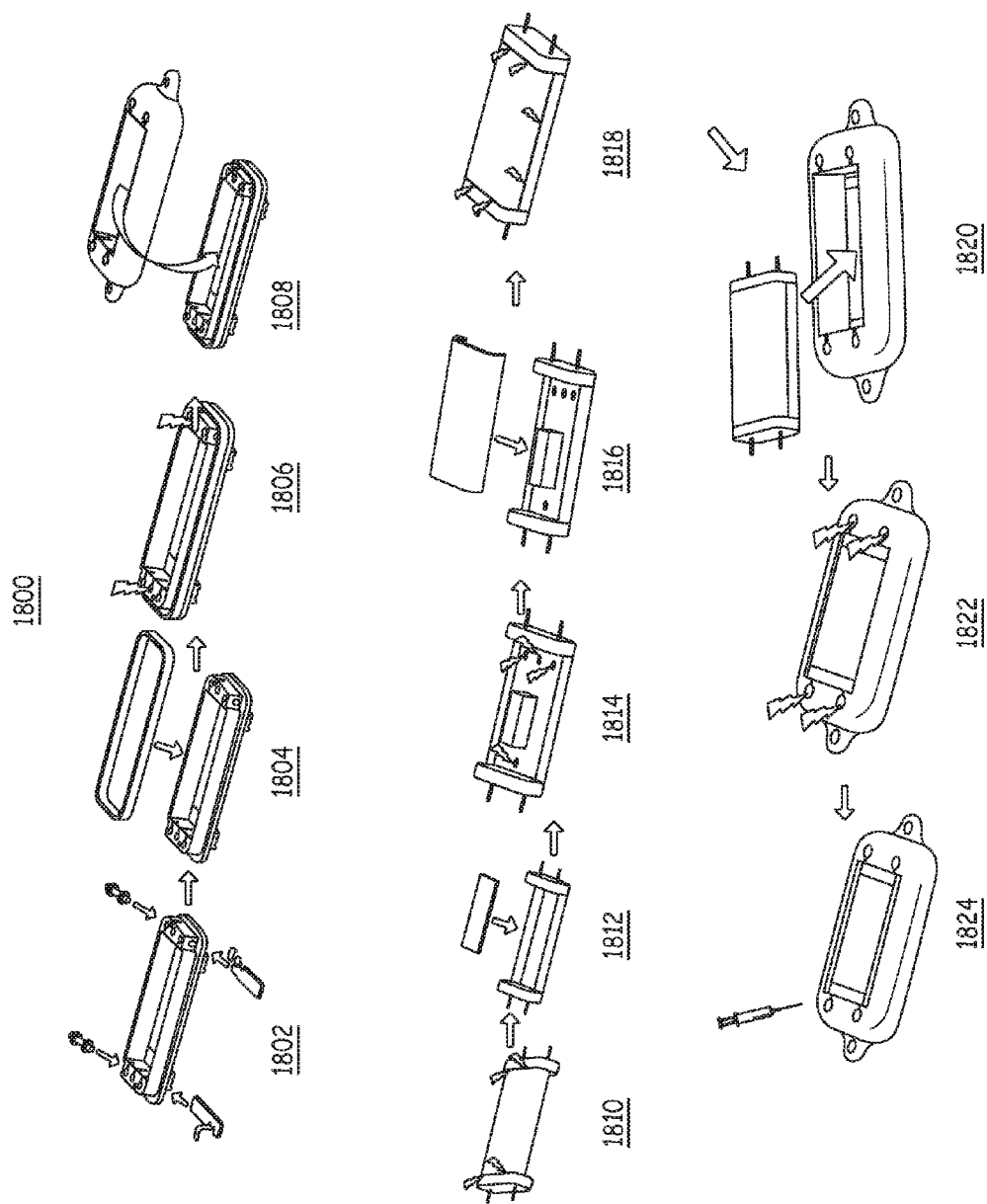
FIG. 37 is a schematic diagram of an exemplary IMD assembly process according to one embodiment.

FIG. 37 is a schematic diagram of an IMD assembly process 1800 according to one embodiment. Process 1800 involves assembling an overmolded inductive coil assembly (steps 1802 through 1808), assembling an IMD housing and internal circuitry assembly (steps 1810 through 1818), and assembling the overmolded inductive coil assembly with the housing and circuitry assembly (steps 1820 through 1824). While the steps of process 1800 are shown in a particular order, it is understood that in some embodiments the orders of steps 1802 through 1824 may be altered and some steps may be omitted or added to provide a final IMD assembly in other embodiments.

At step 1802, a coil mandrel is assembled with feedthrough interconnects. An inductive coil is assembled over mandrel at step 1804 and interconnects are welded or soldered to the coil ends at step 1806. A polymer enclosure is molded or fitted over the coil and mandrel at step 1808 to complete an overmolded inductive coil assembly.

At step 1810 end cap feedthrough assemblies are welded to a first housing portion, which may be machined, molded or stamped. At block 1812 an insulating liner is placed in the first housing portion, and an electronic circuit board is welded to the interior of first housing portion at step 1814. A second housing portion, which may be a machined, molded or stamped portion configured to mate with the first housing portion along minor sidewalls, is assembled with the first housing portion and end cap at step 1816 and seam welded at step 1818 to complete the housing and circuitry assembly.

The housing and circuitry assembly is positioned in the overmolded coil assembly at step 1820. The overmolded coil assembly forms a polymer enclosure circumscribing the first and second housing portions along the welded joint between the mated minor sidewalls of the first and second housing portions. Coil interconnects are welded to feedthrough pins at step 1822. Apertures formed in the overmold assembly to facilitate interconnect welding are sealed with a polymer adhesive or other sealant at step 1824 to complete the IMD assembly process 1800. In this embodiment, electrodes for delivering a neurostimulation therapy may be formed as uninsulated portions of the first and/or second housing portions.

Thus, various embodiments of a minimally invasive IMD housing and methods of manufacturing have been presented in the foregoing description with reference to specific embodiments. The various embodiments of IMD housings described herein are associated with manufacturing methods that can result in a device of reduced size and/or cost. It is appreciated that various modifications to the referenced embodiments may be made without departing from the scope of the disclosure as set forth in the following claims.

The invention claimed is:

1. An implantable medical device, comprising:
   an electronic circuit;
   a housing enclosing the electronic circuit and comprising a joint;
   a polymer seal positioned within the joint to create a hermetic seal; and
   a polymer enclosure member circumscribing the housing and surrounding the joint.

2. The device of claim 1, wherein the polymer enclosure member comprises a protruding structure to facilitate fixation of the medical device.

3. The device of claim 1, further comprising an electrode along an outer surface of the housing.

4. The device of claim 1, further comprising:
   a conductive coil for receiving inductively coupled energy positioned around an exterior surface of the housing and electrically coupled to the electronic circuit,
   the polymer enclosure member surrounding the coil.

5. The device of claim 4, further comprising a mandrel positioned around the housing exterior surface, the coil positioned around the mandrel.

6. The device of claim 1, further comprising:
   a conductive coil for receiving inductively coupled energy positioned around an exterior surface of the housing and electrically coupled to the electronic circuit;
   the polymer enclosure member comprising a first polymer enclosure member surrounding the joint and a second polymer enclosure member surrounding the first polymer enclosure member and the coil.

7. The device of claim 6, further comprising a mandrel extending around an exterior surface of the housing, the coil positioned around the mandrel.

8. The device of claim 6, further comprising an electrode coupled to the housing and exposed through the second polymer enclosure member.

9. The device of claim 6, wherein the coil is positioned around an exterior surface of the first polymer enclosure member.

10. The device of claim 1, further comprising:
    a first housing portion and a second housing portion each comprising a pair of opposing minor sidewalls separated by a major sidewall, the pairs of opposing minor sidewalls of each of the first housing portion and the second housing portion configured to mate along the joint; and
    an end cap assembly coupled to an end of the first housing portion and the second housing portion mated along the joint to define an interior cavity to enclose the electronic circuit.

11. The device of claim 10, further comprising:
    a conductive coil for receiving inductively coupled energy extending around an exterior surface of the housing,
    wherein the end cap assembly comprises an electrical feedthrough coupled to the electronic circuit and to the conductive coil,
    the polymer enclosure member surrounding the conductive coil and the joint.

12. The device of claim 11, wherein the polymer enclosure member comprises an aperture for exposing a connection between the conductive coil and the electrical feedthrough to enable welding of the connection.

13. The implantable medical device of claim 1, wherein the joint is a crimp joint.

14. A method for assembling an implantable medical device comprising:
    enclosing an electronic circuit within a housing comprising a first housing portion, a second housing portion, a joint coupling the first housing portion to the second housing portion, and a polymer seal positioned between the first housing portion and second housing portion in the joint to create a hermetic seal; and
    surrounding the joint with a polymer enclosure member such that the polymer enclosure circumscribes the housing.

15. An implantable medical device, comprising:
    an electronic circuit;
    a housing enclosing the electronic circuit and comprising a first housing portion, a second housing portion and a joint coupling the first housing portion to the second housing portion;
    a polymer seal joining the first housing portion and the second housing portion positioned to create a hermetic seal at the joint; and
    a polymer enclosure member surrounding the hermetic seal at the joint.

16. The implantable medical device of claim 15, wherein at least one of the housing portions is a cofired ceramic.

17. The implantable medical device of claim 16, further including a telemetry coil.

18. The implantable medical device of claim 17, wherein the telemetry coil is cofired into the ceramic.

19. The implantable medical device of claim 18, wherein the telemetry coil is directly cofired into the housing by a metallizing layer.

20. The implantable medical device of claim 16, wherein at least one electrode is cofired into the ceramic.

21. The implantable medical device of claim 20, wherein the at least one electrode is located on an outer surface of the housing.

22. The implantable medical device of claim 15, further comprising a telemetry coil, wherein the housing is a ceramic material and the telemetry coil is inside the housing.

23. The implantable medical device of claim 15, further comprising a telemetry coil, wherein the housing is a metal material and the coil is outside the housing.

24. The implantable medical device of claim 15, wherein the joint is a crimp joint.

* * * * *